US006397190B1

(12) United States Patent
Goetz

(10) Patent No.: US 6,397,190 B1
(45) Date of Patent: May 28, 2002

(54) VETERINARY MEDICATION MONITORING SYSTEM AND APPARATUS

(76) Inventor: Gerald E. Goetz, 15304 Sisson Rd., Penn Valley, CA (US) 95946-9535

(*) Notice: Subject to any disclaimer, the term of this patent is extended or adjusted under 35 U.S.C. 154(b) by 0 days.

(21) Appl. No.: 09/330,934

(22) Filed: Jun. 11, 1999

Related U.S. Application Data

(63) Continuation-in-part of application No. 09/261,044, filed on Mar. 2, 1999, which is a continuation-in-part of application No. 09/260,936, filed on Mar. 2, 1999.
(60) Provisional application No. 60/093,753, filed on Jul. 22, 1998.

(51) Int. Cl.$^7$ ................................................ G06F 17/60
(52) U.S. Cl. ........................ 705/3; 705/2; 702/177; 368/10; 235/375
(58) Field of Search ...................... 705/2, 3; 702/177; 368/10; 235/375

(56) References Cited

U.S. PATENT DOCUMENTS

| 4,588,303 A | | 5/1986 | Wirtschafter et al. .......... 368/10 |
| 4,695,954 A | * | 9/1987 | Rose et al. ..................... 21/15 |
| 4,712,460 A | * | 12/1987 | Allen et al. .................... 83/208 |

(List continued on next page.)

FOREIGN PATENT DOCUMENTS

| JP | 408131405 A | * | 5/1996 | ........... G06F/19/00 |
| JP | 408263562 A | * | 10/1996 | ........... G06F/17/60 |

OTHER PUBLICATIONS

Bridges, Alan J. "Physical Diagnosis Clinical Examination", JAMA, Aug. 12, 1998.*
Mertens et al., Owner Compliance in veterinary medicine: Canine and feline behaviour therapy, Tieraerztliche Umschau, Dec. 1997.*

(List continued on next page.)

Primary Examiner—Vincent Millin
Assistant Examiner—Jagdish Patel
(74) Attorney, Agent, or Firm—John R. Wahl; Merchant & Gould

(57) ABSTRACT

A veterinary medication management system which includes two or three separate components to assist a handler/owner control, monitor and manage administration of prescribed medications to an animal patient. The system comprises a handler/owner component having a retrievable animal and handler/owner database of animal medical history, prior prescribed medications and current prescribed medications, and it includes a data transfer interface, e.g., a hardwired interface, such as an RS232 interface or infrared data transfer port. The system also includes a veterinarian component having a retrievable veterinarian's database of medication information and an input/output device enabling a prescribing veterinarian to enter prescription information into the veterinarian component. The veterinarian's database is capable of receiving and storing handler/owner data transferred from the handler/owner component through said data transfer interface. The system finally also includes a veterinarian support component resident on a veterinarian's computer. The veterinarian's computer is adapted to interface with said handler/owner component to transfer prescription data to said veterinarian support component. At least one of or each of the veterinarian component and the veterinarian support component has the capability of searching a medication database to determine potential medication interactions with currently prescribed medications and identify those to the veterinarian for selective downloading to the handler/owner component so that the handler/owner can be alerted to the potential interactions. The handler/owner component has a scheduler which tracks a plurality of medication dose schedules and includes alarm functions to prompt a handler/owner to administer particular medications to the animal, reschedule them, and/or alert the handler/owner to potential interactions between medications and/or provide caution information to the handler/owner for administration of the medication to the animal.

56 Claims, 23 Drawing Sheets

U.S. PATENT DOCUMENTS

| | | | | |
|---|---|---|---|---|
| 4,860,899 A | * | 8/1989 | McKee | 206/534 |
| 4,926,572 A | | 5/1990 | Holmes | 40/448 |
| 4,970,669 A | | 11/1990 | McIntosh et al. | 364/569 |
| 5,099,424 A | * | 3/1992 | Schneiderman | 705/3 |
| 5,157,640 A | | 10/1992 | Backner | 368/10 |
| 5,200,891 A | | 4/1993 | Kehr et al. | 364/413.01 |
| 5,239,491 A | | 8/1993 | Mucciacciaro | 364/569 |
| 5,289,157 A | | 2/1994 | Rudick et al. | 340/309.15 |
| 5,408,443 A | | 4/1995 | Weinberger | 368/10 |
| 5,547,878 A | * | 8/1996 | Kell | 436/111 |
| 5,602,802 A | | 2/1997 | Leigh-Spencer et al. | 368/10 |
| 5,691,932 A | * | 11/1997 | Reiner et al. | 368/10 |
| 5,772,585 A | | 6/1998 | Lavin et al. | |
| 5,781,442 A | | 7/1998 | Engleson et al. | |
| 5,867,821 A | * | 2/1999 | Ballantyne et al. | 705/2 |
| 5,908,788 A | * | 6/1999 | Kell | 436/111 |
| 5,924,074 A | * | 7/1999 | Evans | 705/3 |
| 6,014,631 A | * | 1/2000 | Teagarden et al. | 705/3 |
| 6,055,506 A | * | 4/2000 | Frasca, Jr. | 705/3 |
| 6,073,106 A | * | 6/2000 | Rozen et al. | 705/3 |

OTHER PUBLICATIONS

*About HIMSS*, 3 page printout of from http://www.himss.org, Sep. 9, 1998.

Resistant Strain: Healtheon Struggles In Efforts to Remedy Doctor's Paper Plaque, *The Wall Street Journal*, Oct. 2, 1998.

Highest Capacity Smart Cards Are Now From Cardiogix, 2 page printout of web sit, Sep. 4, 1998.

Leading Medical Information Technology into Y2K, *Military Medical Technology*, Feb. 1998.

Industry Interview—David Brooks, Group Senior Vice President, SAIC Federal Health Care Group, *Military Medical Technology*, vol. 2, Issue 4.

Is This Any Way to Run a Drugstore?, *MMT (Military Medical Technology)*, vol. 2, Issue 4.

MediCard Information from PC Pay Systems web site, Apr. 19, 1998.

Multi–Prescription Reminder, http://www.mitsi,com, Feb. 25, 1998.

Electronic Reminders, http://www.medportinc.com, Mar. 2, 1998.

What is An e–pill Kinder Reminder?, http://www.viamall.com, Mar. 2, 1998.

REX PC Companion, web advertisement, Mar. 23, 1998.

Nanda Platform, web advertisement, Mar. 23, 1998.

Doctor PalmPilot web advertisement, Thomas Jefferson University web site, Mar. 9, 1998.

Pocket PDR Medical Book System, web advertisement, Mar. 23, 1998.

Cardiogix Health Data Card Streamlines Care, Cuts Costs, press release from http://www.cardiogix.cm, Sep. 4, 1998.

Highest Capacity Smart Cards Are Now from Cardiogix, press release from http://www.cardiogix.com, Sep. 4, 1998.

Health Data Card Family, http://www.cardiogix.com, Sep. 4, 1998.

Data Packets advertisement, *Militay Medical Technology*, Feb. 16, 198.

VAQTA advertisement.

Smart Cards, www.cardiogix.com, Sep. 2, 1998.

New Payday for Rural Mexico: Coin Bags Are Out, Platic Is In, The Wall Street Journal, undated.

PalmPilotWorkPad information from http://www.timewarner.com, Mar. 9, 1998.

Eric's PalmPilot Health Care Database, http://www.pathcom.com, Mar. 9, 1998.

Medical Communication Systems—Products, http://www.medcomsys.com, Mar. 9, 1998.

Plastic Dog Tags?, *Machine Design*, Oct. 8, 1998.

Prescription Dedication, Combining Drugs Safely Takes a Doctor–Patient Partnership, *Rocky Mountain News*, Sep. 1, 1998.

RxPhenom web advertisement, Sep. 3, 1998.

Franklin Medical Division advertisement for Nursing Organizer and Pocket PDR Medical Book System.

Vials of the Dolls—The New Market in Adherence Devices, http://www.thebody.com, Jan. 26, 1999.

Drug–Reax System: Details, http://www.micromedex.com, Jan. 28, 1998.

Storm brews over 'health identifier' plan The New York Times.

Plans for new health ID system under fire, The New York Times.

Trip Report for G–7 Healthcare Data Card Meeting and Healthcard 95 Conference in Frankfurt Germany; http://www.va.gov/card/g7–9602.htm.

About HMSS: http://www.himss.org/about/index.htm.

Cardlogix Creates More Smart Card Options; http://www.cardiogix.com/press8.html.

Health Data Card Family; http://www.cardiogix.com/health.html.

Healthcare Data Cards in North America, Daniel L. Maloney, Director, Technology Innovations Department of Veterans Affairs, Silver Springs, MD, USA; maloney.dan@forum.va.gov;http://www.va.gov/card/.

Frank K. Wood's Healthadvisor; The Conspiracy of Silence About Prescription Drug Side Effects, Fall 1997.

Local Firm Gets Pharmacy Deal, Sacramento Business.

* cited by examiner

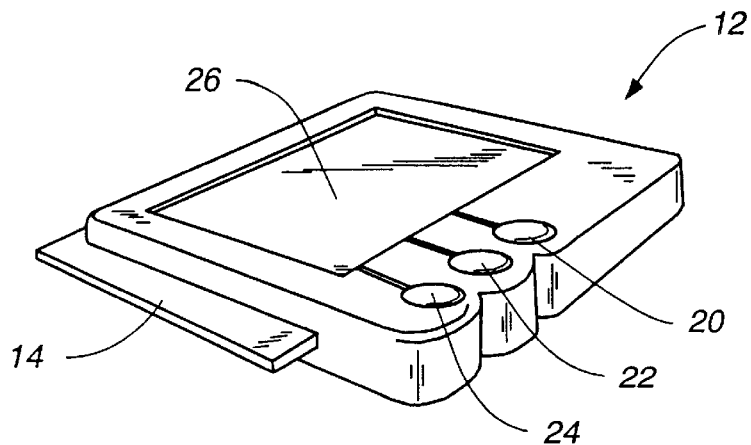
Fig. 2
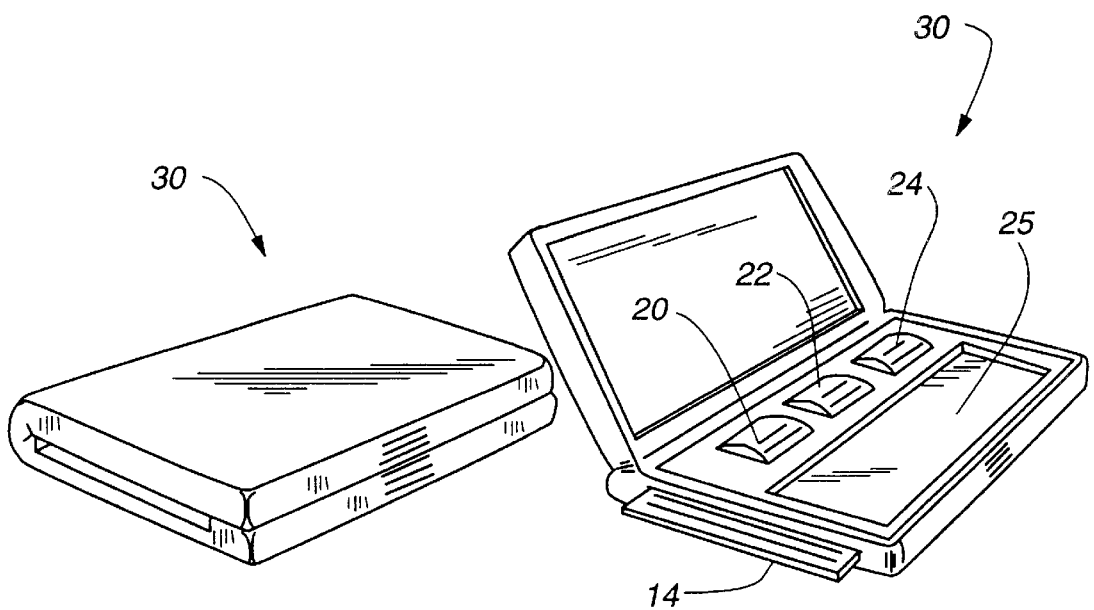
Fig. 3A  Fig. 3B

Fig. 12

CHIQUITA
HANDLER/OWNER: BOB SMITH

| Prescription | Medical | Contacts | User |

| Priority ▼ | Type | Name |
|---|---|---|
| EMERGENCY | Handler/Owner | Bob Smith |
| | Veterinarian 1 | John Abrams D.V.M. |
| | Veterinarian 2 | Bill Binkley D.V.M. |
| | Emergency 2 | Betty Smith -Wife |

(hm)(123)456-7890, (wk)(123)456-7899;
1234 Barbery Lane, Somewhere, CO 80524

Fig. 11

CHIQUITA
HANDLER/OWNER: BOB SMITH

| Prescription | Medical | Contacts | User |

| Date ▼ | Condition | Source |
|---|---|---|
| | !!ALLERGIES!! | |
| 12/12/98 | Myo Infarc | Abrams |
| 09/08/98 | Stomach Virus | Jones |
| Family | Liver Disease | Smith |
| Family | Blood Disorder | Smith |

2 distant relatives with Hepatolinticular Degeneration. Lead to death.

VETERINARY MEDICATION MONITORING SYSTEM AND APPARATUS

CROSS-REFERENCE TO RELATED APPLICATIONS

This application is a continuation-in-part of U.S. Nonprovisional patent application Ser. No. 09/261,044, entitled MEDICATION MONITORING SYSTEM AND APPARATUS, filed Mar. 2, 1999 which is a continuation in-part of U.S. Nonprovisional patent application Ser. No. 09/260,936, entitled MEDICATION MANAGEMENT APPARATUS, filed Mar. 2, 1999 and claims the benefit of priority of the filing date of U.S. Provisional Patent Application Serial No. 60/093,753 entitled POCKET DOCTOR, filed Jul. 22, 1998.

BACKGROUND OF THE INVENTION

1. Field of the Invention

This invention pertains to a veterinary medical information product which is maintained and controlled by the handler or owner of the animal to which the information pertains.

2. Description of the Related Art

Veterinary medical science has created many new methods, treatments, and medications to extend and improve the lives of animals. However, this has resulted in a significant increase in the medical information that a person must be aware of in order to maintain their animal's health, and get the best benefit from these medical improvements. Often, a sick domestic or wild animal, and even a healthy animal may be called upon to receive a number of different prescription medications, salves and ointments, and other topical treatments. Each medication typically requires specific instructions, including warnings on correct administration, consumption and alerts for indications of possible side effects. Because there is such a significant increase in the amount of medical information that a person must know in order to optimally treat an animal's condition, errors can occur that adversely affect treatments and/or counteract or minimize the beneficial impact of the medications. At worst, serious injury or death has occurred due to incorrect treatments.

Problems arise when either the veterinarian making the prescription or the person filling the prescription makes an error or provides information that is not understood by one of the other parties. These errors can be from transcription, misinterpretation, or insufficient information being made available to the handler/owner. The most common handler/owner originated errors are:

(a) giving incorrect doses to the animal
(b) giving doses to the animal at the wrong time
(c) forgetting to give a dose
(d) stopping medication too soon
(e) giving or administering the dosage improperly, causing interactions.

SUMMARY OF THE INVENTION

A system in accordance with the present invention includes a device for an animal handler or owner to use to better control implementation of medication therapies. The device will, among other functions, track and display:

(a) medication name & purpose
(b) dosage, frequency and duration
(c) possible side effects
(d) record of medications administered
(e) special instructions for administering medications, such as with giving the medication with or without meals, fluids, avoiding sunlight, etc.

Besides information about medications, it is important for a handler/owner to have a brief medical history that can be provided to veterinarians or other animal care providers, have a log of consumption for their animal's medications, and maintain information about who their veterinarian and/or insurance providers are, and handler/owner personal contact information. This data is considered critical not only during typical interaction with veterinary health care providers, but particularly in emergency medical situations. Any device that is capable of tracking the medication data that a veterinary handler/owner needs should also be capable of tracking all these other health related data.

However, it must be recognized that this medical information loop includes other personnel besides the owner/handler. These include, as an example, veterinarians, breeders and possibly trainers. Thus any device must be capable of allowing each of them to read veterinary information on the animal, handler/owner data, and input information, and it must not require any significant time for them to accomplish this. In particular, the system must blend with day to day activities of the veterinary health care provider as well as the handler/owner.

Any solution to the problem must recognize this veterinary medical information chain that primarily consists of the animal, the handler/owner, and the health care prescriber (typically the veterinarian) and care provider (for example, the trainer). The information in this chain is created preferably on a per animal or set of animals basis, making the handler/owner the natural repositor for the information, with the prescriber (the veterinarian) being the initiator of the information and being a source of complementary information so it is in a form useful to the handler/owner. Thus the product must work with both veterinary medical terminology and layman's terms to promote optimum benefit of treatments and medications.

An additional requirement of any product that contains veterinary medical history information on an animal, especially in professional animal breeding and care, is security. Thus any product must provide maximum protection of data from access by unauthorized persons. Although many devices use PIN's to limit access and a PIN or password would be necessary for this product, the nature of the data in a device such as proposed here may also protect the data via encryption.

The present invention is a system of component devices that provides proper information to the handler/owner of the animal so that the handler/owner can ensure that each animal can get maximum benefit from their medications, he or she can track medication consumption, and facilitate transfer of critical data for optimal care of the animal. The system is capable of managing information, in a highly portable form for an individual animal or set of animals cared for by a handler/owner. The system in accordance with the present invention performs and/or facilitates the following functions:

(a) Provides a record of medication information;
(b) Maintains current and historical veterinary medical data on the animal handler/owner;
(c) Creates and maintains a historical log of veterinary pharmaceutical agent consumption;
(d) Warns handler/owner of side effect indications, interactions, and other special instructions, especially when scheduled medication times are missed or modified; and (e) Provides a vehicle for interchange data among various individuals and groups involved in animal care such as the handler/owner, veterinarian, veterinary technician, emergency personnel and veterinary hospital personnel.

BRIEF DESCRIPTION OF THE DRAWINGS

This invention will be more fully understood by reference to the following drawings which are for illustrative purposes only:

FIG. 2 is a perspective view of one embodiment of a handler/owner component of the system in accordance with the invention.

FIG. 3 is a perspective view of an alternative embodiment of the handler/owner component of the system in accordance with the invention.

FIG. 11 is a medical history screen for the animal identified in FIG. 9 showing the animal's family medical history.

FIG. 12 is a contact screen for the animal identified in FIG. 9 showing handler/owner and/or trainer contact information.

DETAILED DESCRIPTION OF THE INVENTION

First Embodiment

Figure 1:
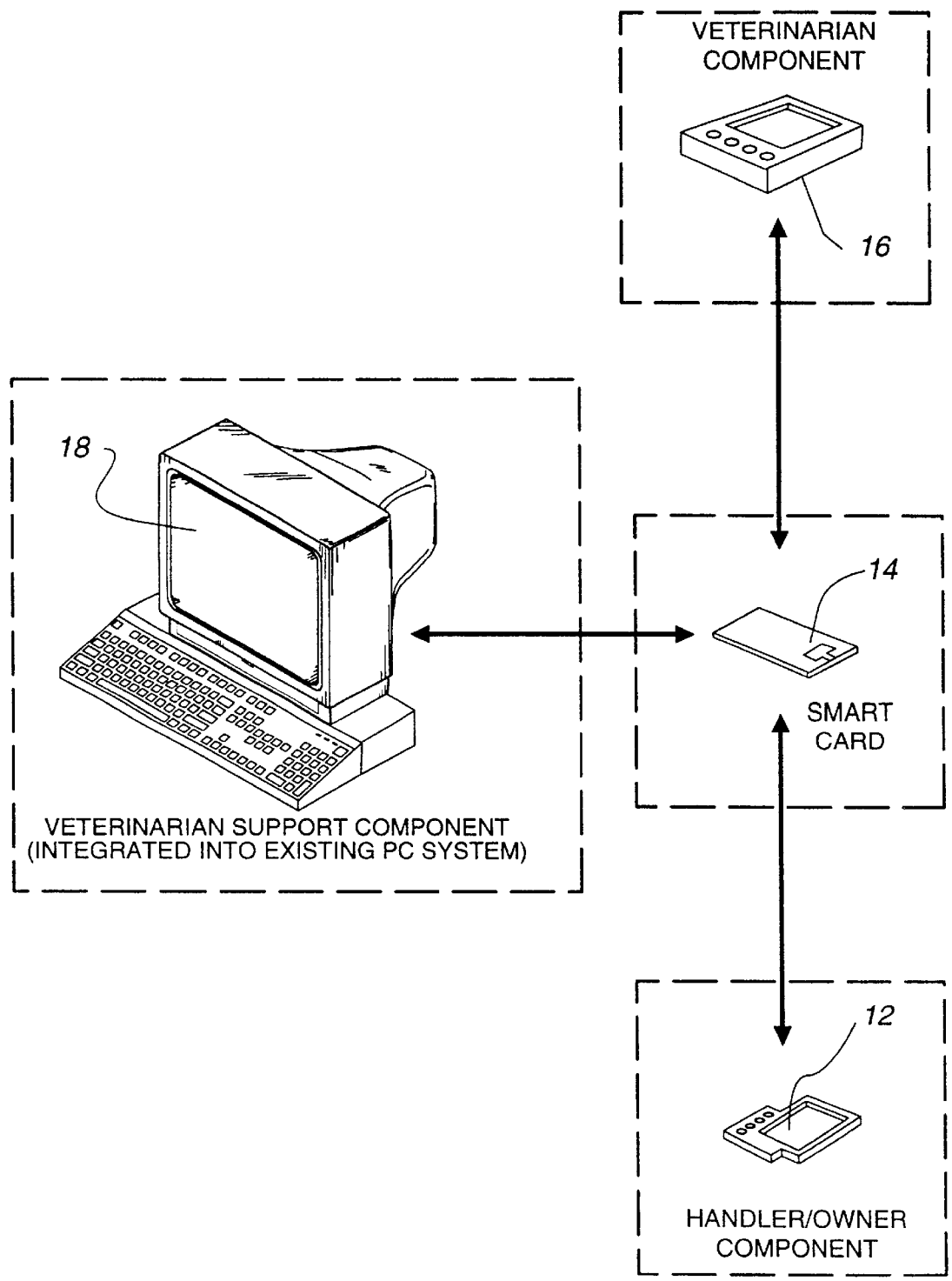
FIG. 1 is a functional system block diagram of a first embodiment of the veterinary medication management system according to the present invention.

A first embodiment of the present invention is shown functionally in FIG. 1. The system 10 comprises preferably three separate components that share a common database, where the database may be resident in the handler/owner component 12 or contained on a memory device 14 such as a smart card. The three components of the system 10 in accordance with the present invention are a handler/owner component 12, a veterinarian component 16, and a veterinarian support component 18. It is to be understood throughout this description that the veterinary component 16 and support component 18 may be combined into one veterinary component as the veterinarian's needs dictate.

As currently embodied, the memory device 14 is a smart card, which is an integrated circuit or chip containing a microprocessor, ROM, RAM, and EEPROM, packaged within a plastic panel much like a credit card. The memory device 14 could be manifested in a variety of other forms as well. For example, the memory device 14 may be replaced by a simple memory card which relies on the processor in one of the three components such as the handler/owner component 12 in order to operate.

Handler/Owner Component

The handler/owner component 12 is preferably a generally rectangular battery powered unit that has several input buttons 20, 22, and 24 along a bottom edge thereof, an LCD panel 26 visible on a front surface of the housing, and a scroll switch 28 preferably located on one edge of the housing which permits the handler/owner/user to scroll backward and forward through the various display screens and options on the LCD as will be subsequently described. The handler/owner component 12 basically provides the following basic functions:

1. Displays the medical data contained on the memory device or, in the smart card shown, by reading the EEPROM on the memory device 14. The display may include an ambient light sensor to adjust the contrast of the display and/or backlight of the display automatically depending on ambient light conditions.
2. Allows the handler/owner to scroll through the data using various means to indicate, via a typical graphical user interface menu, which type of data is to be displayed.
3. Maintains date and time information.
4. Provides an alarm for when an event, such as required consumption of a medication, is to occur. The alarm can be visual, aural, or tactile.
5. Indicates dosage, frequency, special considerations in consuming the medication.
6. Provides a means to identify the type of pill to be taken such as a graphic image of the medication to be administered. (a red cylindrical pill, a blue heart shaped pill, etc.)

7. Provides information about correct consumption of the medication, including possible side effects and potential interactions with other drugs and/or consumables such as food, water, milk, etc.
8. Provides a means for input by the handler/owner via input buttons 20, 22, and 24, to indicate whether an alarmed event (e.g., time to administer a medication) was accepted or delayed, and log the time, date, and action for that alarm.
9. Provides power to perform the above functions, as the smart card typically does not contain any power source of its own.
10. Is portable such that it can be carried by the handler/owner at all times, such as in a pocket, purse, or worn with a strap on an arm, around the neck or waist. The handler/owner component may also be provided with various attachment means, such as a magnet or hook and loop fabric to attach the unit conveniently to nearby and/or highly visible surfaces, depending on the preferences of the handler/owner.
11. Provides security, via coding features and data encryption, to prevent unauthorized use and access to the data encoded on the smart card or within the handler/owner component.

Two example physical configurations of the handler/owner component are shown in FIGS. 2 and 3. The system allows a variety of devices to be used, but each one must have the capabilities to perform the prescribed unique functions. In the case of FIG. 2, the device has a slot to accept the memory device 14 or smart card, and only requires 3 buttons 20, 22, and 24 to access the data, or to prompt the handler/owner to respond to the event alarm. The handler/owner component 12 alarm may be audible, visual or tactile as in a vibrator device. FIG. 3 shows a device 30, much like a woman's compact, that contains a larger display area, such that an elderly handler/owner with reduced visual acuity can still use the handler/owner component. Each of these embodiments 12 and 30 preferably will include a button or switch control to permit the handler/owner to scroll through display screens and an ambient light sensor coupled to the LCD to automatically adjust the contrast and back light for the display depending on ambient light conditions upon activation by the handler/owner or the activation of an alarm event.

Veterinarian Component

The veterinarian component 16 is preferably a hand held personal digital assistant device such as a Palm PC or Palm Pilot type device that receives the memory device 14 and reads and writes data from and to the memory device 14. The veterinarian component 16 is preferably programmed with at least the following basic functions:

1. Displays the medical data contained in the smart card by reading the EEPROM on the memory device 14.
2. Contains data specifically tailored for use by the veterinarian, such as a database of diagnoses and common illnesses and correlated potential medications that may be prescribed, and a library of special instructions or treatments to be performed by the handler/owner that the veterinarian may prescribe.
3. Writes data to the handler/owner's memory device 14 when it is docked in the veterinarian component 16.
4. Optionally may include a special enclosure configuration for the use of the component 16 in areas where blood born pathogens are a concern, e.g., emergency rooms and surgical suites.

Veterinarian Support Component

The veterinarian support component 18 is essentially a smart card reader and a software application resident on the veterinarian's personal computer in his or her office or clinic which reads the veterinarian prescription data from the memory device 14 and correctly formats the veterinarian prescribed prescription data recorded on the memory device 14 in a form useable to the handler/owner. This software application will reside on the same personal computer (PC) that the veterinarian currently utilizes. The time and effort for the veterinarian to provide this medication data to the handler/owner in the handler/owner component is designed to be very minimal, typically on the order of 15–30 seconds or less.

Nearly all veterinarians now have a personal computer in their clinic pharmacy. Potentially the computer may be set up to have links to various animal health organizations, in particular organizations that provide data on both prescription and OTC medications for both humans and other animals. There is a code, known as the National Drug Code (NDC) that identifies every medication sold in the United States for human consumption. There is also a Veterinarian's Drug Reference, published by Pharma Vet Publishing Co. which provides drug information for veterinary medical use. In combination with this code and the access to various networked databases, and the Drug Reference, the veterinarian can access and supply necessary information about the prescribed medication for the animal to the handler/owner. Today, for drugs with FDA approval, this data is typically printed on a sheet that contains common uses, consumption requirements, cautions and possible side effects of the particular medication in humans. This information as well as complementary information on other veterinary medications would be stored in the veterinarian's support component 18 (the PC), or could alternatively be included directly in the veterinarian component 16. Thus the veterinarian support component 18 in the system 10 of the present invention, through the veterinarian's PC, reads and writes data from the veterinarian's database to the memory device 14 , and will typically supply the data that is conventionally printed on the prescription information sheet to the memory device 14 in addition to medication administration instructions.

The system 10 in accordance with the first embodiment of the invention uses smart card technology to make the link between the three easy, quick, and secure. The components may alternatively communicate via infrared serial communication links, or other communication methods such as the recently developed Personal Area Network (PAN) rather than a smart card. However, in the first preferred embodiment, a memory device 14 is utilized as the data transfer medium for illustration purposes.

Figure 4:
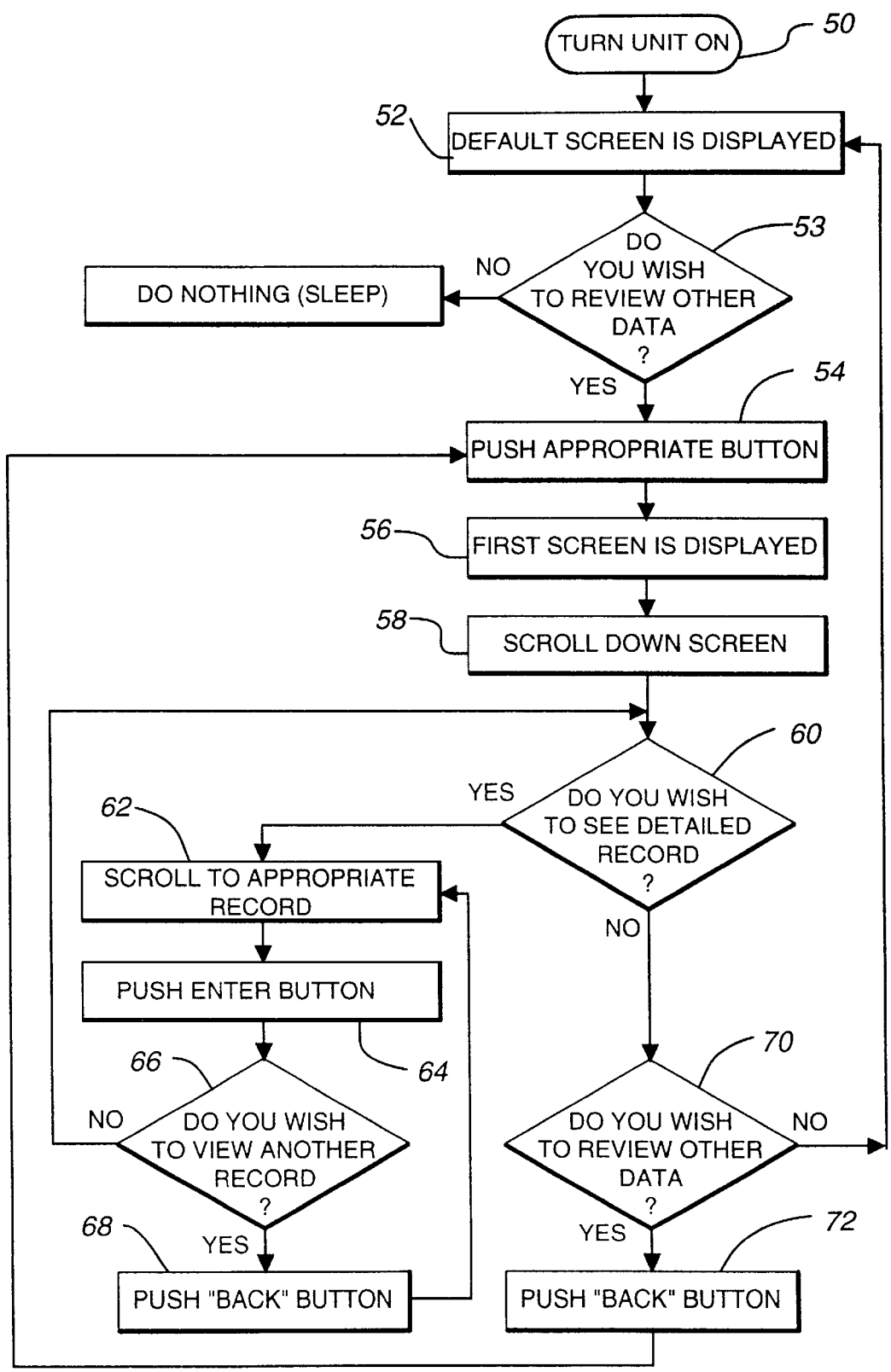
FIG. 4 is a flow diagram of the software operation of the handler/owner components shown in FIG. 2 and FIG. 3.
Figure 5:
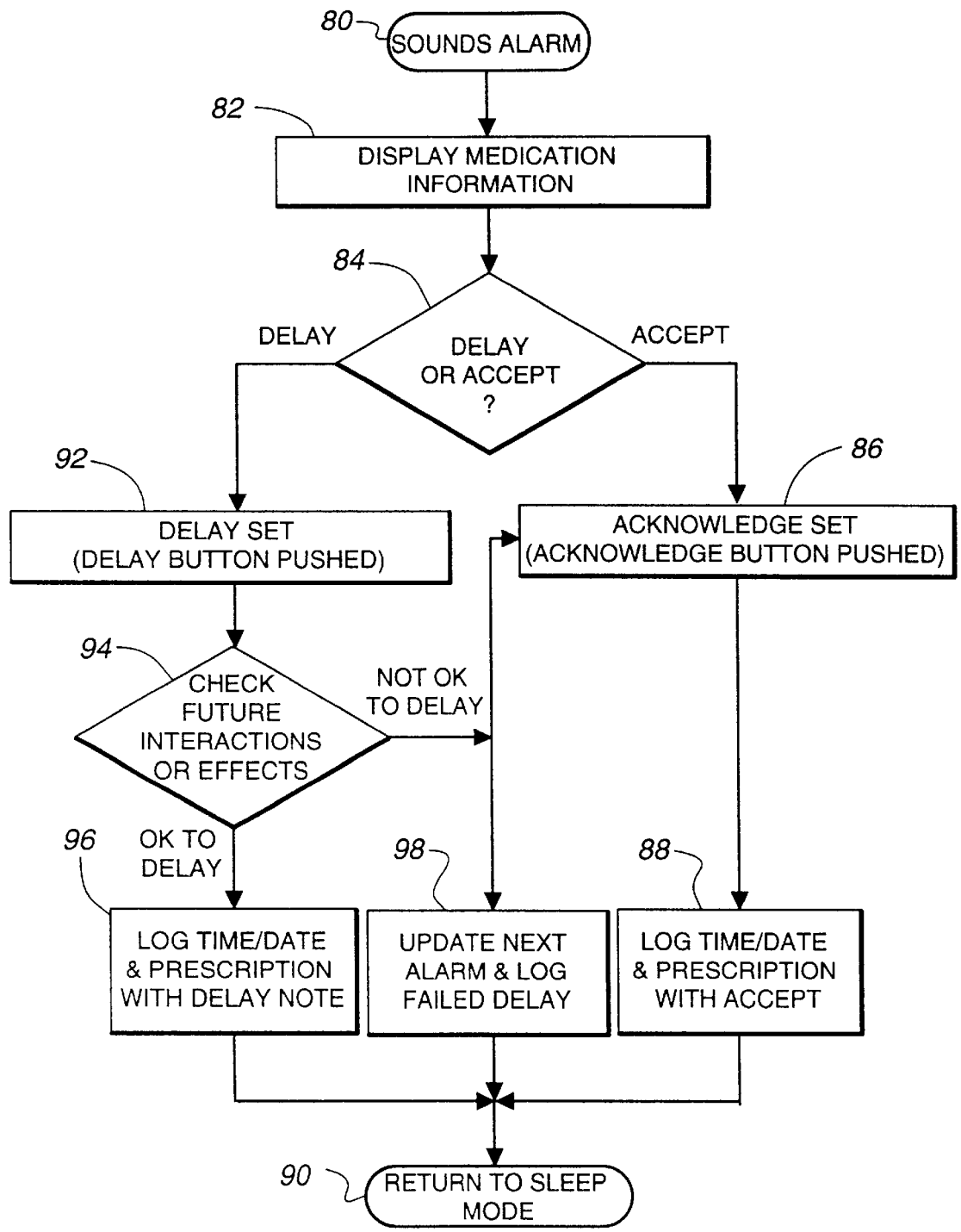
FIG. 5 is a flow chart showing a method of responding to an alarm from a handler/owner component in accordance with the present invention.

The memory device 14 will contain at least the following data about the handler/owner:

1. Handler/owner Identification Information
   1.1. name of animal or animals
   1.2. breed, age, weight, height of each animal
2. Handler/Owner Contact Information
   2.1 names, address, phone number
   2.2. Trainer name address, phone number
3. Veterinarians
   3.1. Names & affiliation or specialties
   3.2. all phone numbers and addresses
4. Insurance Information
   4.1. Company, plan identification
   4.2. contact phone 5. Animal Medication Consumption History Log
   5.1. Date & time for each medication consumed
   5.2. Date & time for a delayed medication
   5.3. Occurrence of any side effect from a medication
6. Animal Medical Conditions
   6.1. brief history
   6.2. allergies
   6.3. current conditions
   6.4. relevant family or bloodline history
7. Drug data (for every medication consumed) per animal
   7.1. name (trade/generic) indication
   7.2. dosage, frequency, timing
   7.3. interactions
   7.4. side effects
   7.5. special instructions
   7.6. prescribing veterinarian
   7.7. dispensing pharmacy & date filled, if any
8. Other information
   8.1. Advertising messages for product sponsors
   8.2. Special instructions for emergency response personnel
   8.3. Security access information Both of the sample handler/owner devices shown in FIGS. 2 and 3 use the 3 button input configuration to display data and to respond to alarms. A flow diagram of the software algorithm for viewing the data on the device is shown in FIG. 4. The basic algorithm would access the data contained on the memory device 14. To respond to an alarm, a possible sequence of steps for the handler/owner component is shown in FIG. 5. A single animal display example is illustrated. However, multiple animal information may be contained in the handler/owner component. The information and sequences described below and shown in the Figures would be repeated with appropriate information for each animal in the series of screens displayed.

In block 50 the handler/owner component is turned on. Alternatively, the handler/owner component 12 may be configured to always be on and simply placed in a conventional "sleep" mode to conserve battery life when there is no activity or alarm condition. In this situation, block 50 represents the handler/owner taking the unit out of the "sleep" mode by pressing any of the input buttons 20, 22, or 24. Process flow then transfers to operation 52 wherein a default display screen appears on the LCD panel 26. The default display screen may contain general animal identification information, a menu of currently prescribed and active medications, or a listing of current pending scheduled alarm times along with the current date and time. Also on this default screen may be a query 53 asking whether additional data display is desired. If the handler/owner does not desire additional data to be displayed, the default display remains on the LCD for a predetermined amount of time and then the component returns to the sleep mode.

If the handler/owner wishes additional data review, the handler/owner will push, in operation 54 the appropriate input 20, 22, or 24, whichever is indicated by the display 26. Control then transfers to the first display screen 56 which, for example, may be the first medication currently prescribed. In operation 58 the handler/owner scrolls through the screen data until a query 60 appears. Query 60 asks whether the handler/owner wishes to view the underlying record for a particular entry on the screen. If the handler/owner presses the appropriate "yes" input button, control transfers to operation 62 in which the program automatically jumps to the appropriate indicated detailed record. The handler/owner, in operation 64, may then push the appropriate "enter" button to view the detailed record. Control then transfers to operation 66 in which the handler/owner is queried whether another record is to be viewed. If not, control then transfers back to operation 60.

If the handler/owner wishes to view another record, control transfers to operation 68 where the handler/owner presses the "back" button, which transfers control to operation 62 for review of another detailed record. If the handler/owner does not wish to view a detailed record in operation 60, control transfers to operation 70 where the handler/owner is queried whether any other data should be displayed. If not, control transfers back to operation 52 wherein the default screen is displayed for a predetermined period of time, then the component 12 returns to the sleep mode. If the handler/owner answers the query in operation 70 in the affirmative, the "back" push button is indicated, and when pushed, transfers control back to operation 54. In this manner, the handler/owner can review all handler/owner accessible data programmed into the memory device 14 and loaded into the handler/owner component 12.

As previously mentioned, the handler/owner component 12 includes a scheduling and alarm function for the prescribed treatments or medications. The process operations which occur upon an alarm condition are shown in FIG. 5. In operation 80 the internal alarm clock in the handler/owner component 12, when the programmed alarm time equals the current time, sounds an alarm, either visually, audibly or by vibration or a combination of these, taking the component 12 out of the "sleep" mode. Control then transfers to operation 82 wherein the particular prescription information for the precipitating medication alarm is displayed on the LCD screen. This information may be the current time, the scheduled dosage to be taken, the drug name, and possibly a description such as of the shape or color of the pill to be taken. Also, cautions may be displayed on the same screen such as—Do not take with milk—, —Take with food—, or Take only with medication Y—. Control then transfers to operation 84. In operation 84, the handler/owner is asked whether to accept or delay action as required by the information displayed in operation 82. In the event that the handler/owner accepts or acknowledges the action, the handler/owner presses the input button 20, 22, or 24 that is labeled "accept" or "acknowledge" in operation 86. Control then transfers to operation 88 where the time/date and prescription medication is logged with acceptance, i.e. that the handler/owner has administered the prescribed medication to the animal handler/owner at that time. Control then transfers to operation 90 where the handler/owner component 12 returns to the sleep mode until the next alarm condition occurs or the handler/owner requests information as in operation 50 in FIG. 4.

However, if the handler/owner elects to delay administering the particular medication generating the alarm condition at that time to the animal, the "delay set" labeled button is pressed in operation 92. Control then transfers to operation 94 in which the database contained on memory device 14 is queried whether it is permissible to delay. If it is permissible to delay, control transfers to operation 96 where the handler/owner component 12 logs the time and date of this decision with the prescription information and the delay note. A revised alarm time is set and control then transfers to operation 90 where the component 12 returns to the sleep mode. If the program in operation 94 determines that delay is not permissible then the handler/owner is allowed to reconsider. Control then transfers either back to operation 86 permitting the handler/owner to administer the medication as scheduled, i.e., the handler/owner presses the acknowledge button, and log it appropriately or to operation 98 where the handler/owner presses a button labeled "skip" and the failed time and date (i.e. that the handler/owner failed to administer the required dose) is logged. Control then transfers to operation 90 where the component 12 returns to the sleep mode.

Figure 6:
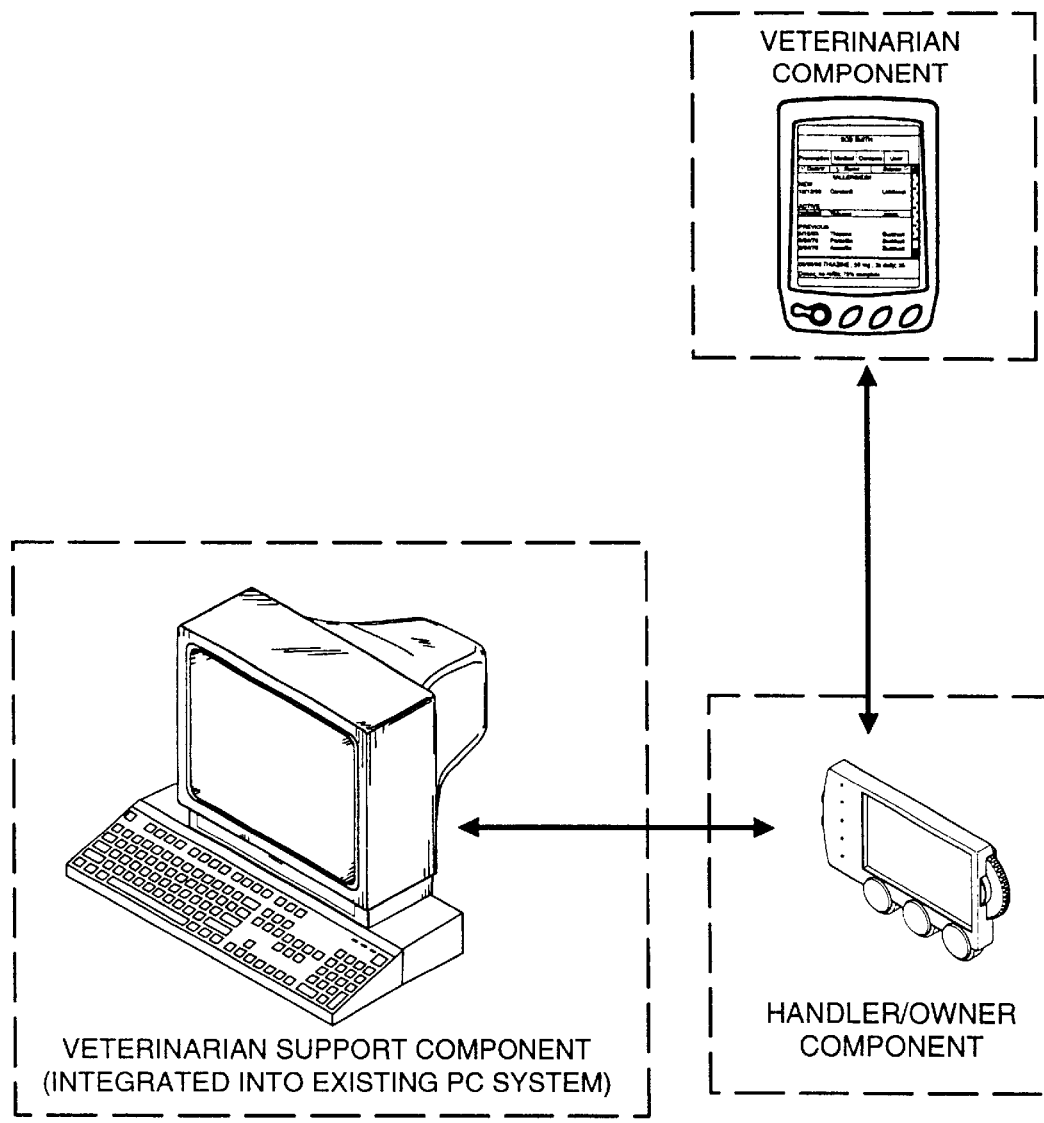
FIG. 6 is a functional system block diagram of a second embodiment of the veterinary medication management system according to the present invention.

The integration of the memory device 14 with this appropriate medical data in the handler/owner component 12 can also be applied to devices that actually contain and dispense the medication. In addition, other medical assistance device adaptations for special needs such as for the hearing or sight impaired are also possible as well as a physical design for handler/owners who are impaired from pressing buttons. In these latter instances, voice input devices may be utilized rather than buttons Second Embodiment Turning now to FIG. 6, a system 100 in accordance with a second embodiment of the invention is shown. In this embodiment, the system 100 eliminates the need for a memory device 14 as in the first embodiment. The system 100 comprises a veterinarian's component 102, which may be embodied in a specially programmed personal digital assistant such as the Palm PC, a handler/owner component 104, and the veterinarian support component 106. The handler/owner component 104 is linked to the veterinarian's component 102 and veterinarian's PC via infrared link or by cable via RS232 interface. Alternatively, the components may also be linked by modem in the situation where the handler/owner and veterinarian are physically separated, yet a modification of prescription is desired by the handler/owner and approved by the veterinarian. Thus there is no need for a smart card as all of the handler/owner information resides in the handler/owner component. The veterinarian component may optionally be connected to an external storage device for archiving the data on the handler/owner component. This optional archive capability may be alternatively provided via the veterinarian support component as the veterinarian may be more accessible to the handler/owner than the veterinarian in many circumstances. However, it is preferred in the present invention that the handler/owner component provide the handler/owner with control and full information on his or her animal's medical condition. This way, should the handler/owner need to see a new veterinarian or become involved in an accident, the veterinarian and/or emergency medical personnel will have always have the necessary information in order to treat the animal appropriately.

Figure 8A:
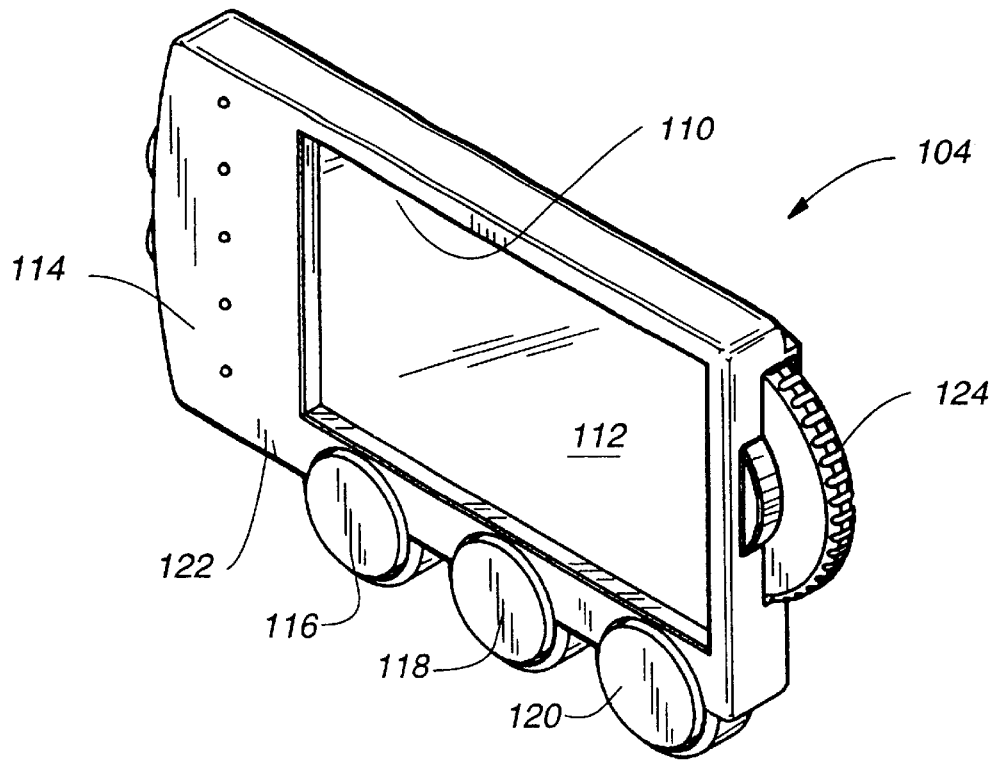
FIGS. 8A and 8B are front and rear perspective views of a handler/owner component of the system according to the present invention shown in FIG. 6.
Figure 8B:
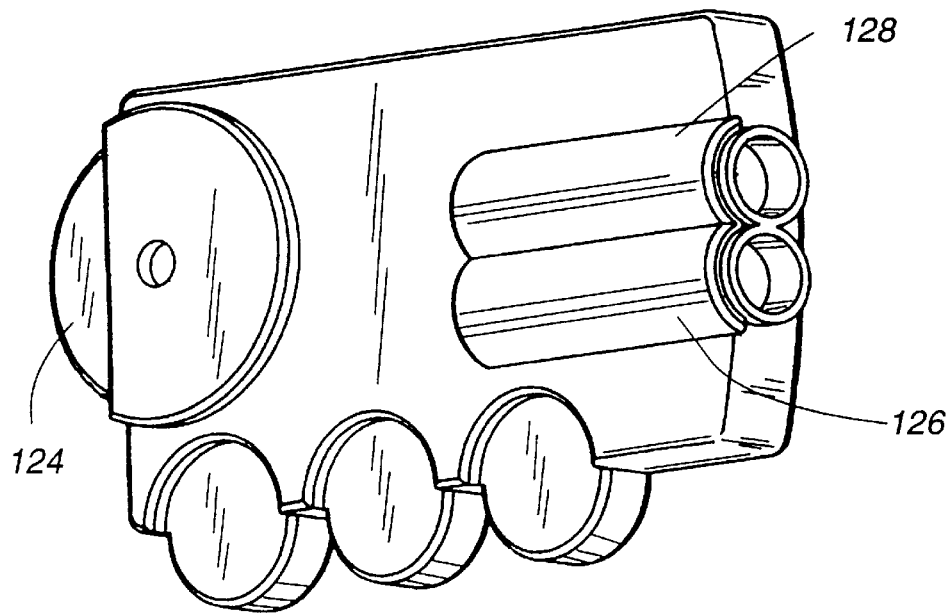

An exemplary handler/owner component 104 is shown in front and rear perspective views in FIGS. 8A and 8B. Handler/owner component 104 comprises a generally rectangular housing 108 that has enclosed within it a central processing unit, memory and electronic circuitry for performing the functions described herein, an alarm clock capable of scheduling and tracking a number of different prescriptions and administration frequencies, a liquid crystal display screen, a power supply, and input devices to permit the handler/owner to interact with the component. As shown in FIG. 8A, the housing 108 includes a window 110 for the LCD screen 112 in a front side 114. A set of three push button controls 116, 118, and 120 are provided along the bottom edge 122 of the housing 108. A rotatable scroll switch 124 is mounted in the housing 108 such that an arcuate portion of the switch 124 projects from the right side of the housing 108. As can readily be seen in the rear view of the component 104 in FIG. 8B, battery compartments 126 and 128 are provided in the housing 108 for two AA size battery cells. The push button switches 116, 118, and 120 are positioned along the bottom edge of the housing 108 so that they may be actuated easily by almost any handler/owner, especially those with limited manual dexterity. The function of each of these buttons changes as the screens on the LCD change. Consequently, the labels for the particular buttons appears in the LCD screens as shown in FIGS. 25 through 43 and as described below. The wheel 124 provided along the right side of the housing 108 is also for convenient operation by a handler/owner's thumb. Other configurations of the handler/owner component may alternatively be provided. The particular configuration shown in FIGS. 8A and 8B is merely one example.

Veterinarian Component

The veterinarian component 102 is preferably essentially a conventional personal digital assistant such as a Palm PC with the Windows CE operating system and particularly programmed for the veterinary medication management system application. FIGS. 9 through 24 show a number of exemplary screens that take the veterinarian through a review of the handler/owner's medical history, contact information, and facilitate the veterinarian's diagnosis of an ailment and assist the veterinarian in arriving at and prescribing an appropriate treatment for the handler/owner's ailment. Note that all names, addresses, etc. that are utilized in the description and Figures are fictional and exemplary only. Any resemblance to any person living or dead is merely coincidental.

Figure 9:
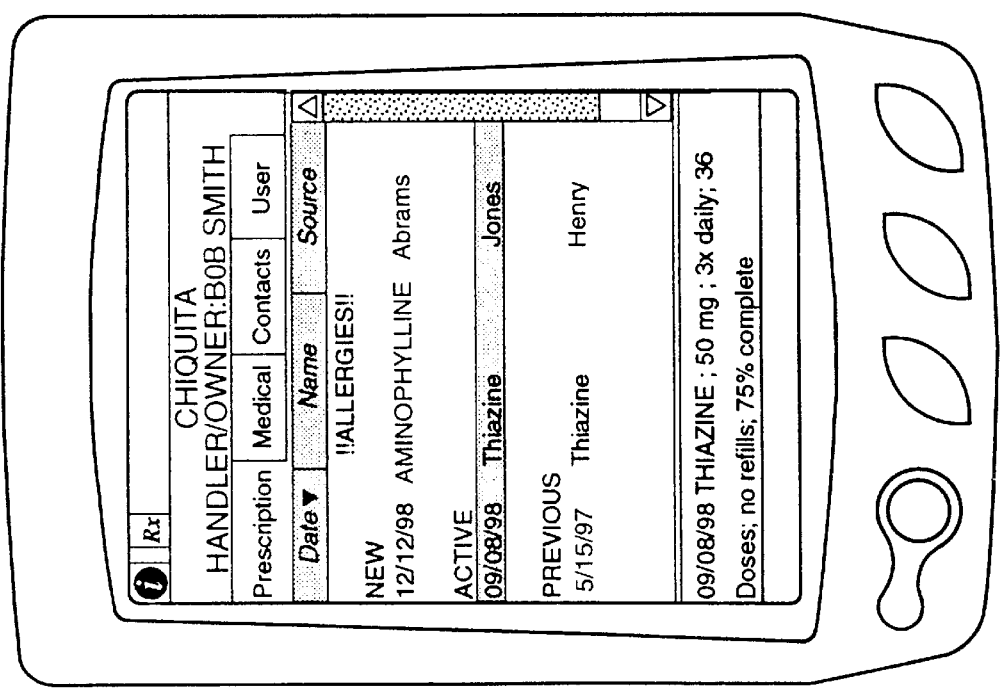
FIG. 9 is a veterinarian component screen showing medication information for a particular animal.
Figure 14:
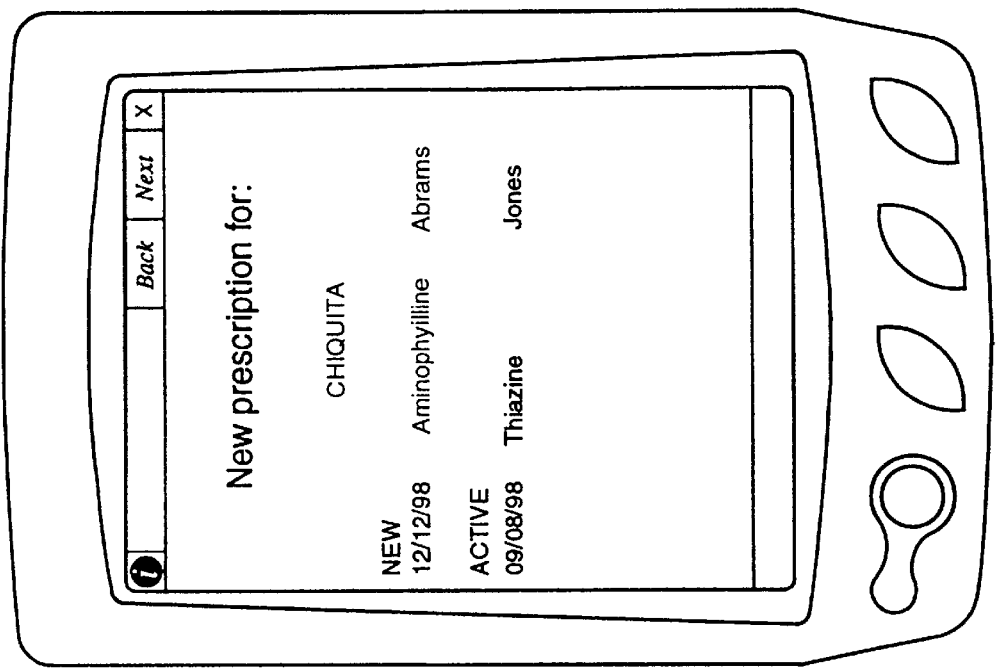
FIG. 14 is a current medication screen for the animal identified in FIG. 9.

Assume that a handler/owner, Bob Smith, comes in to a veterinarian's office with his pet "Chiquita", the pet is examined, and diagnosed with a particular illness. The veterinarian imports data to his or her veterinarian component 102 from the handler/owner's handler/owner component 104. The veterinarian component 102 has four categories of screens as shown in FIG. 9; Prescription, Medical, Contacts, and User. The first screen that pops up is the prescription information screen for handler/owner Bob Smith's pet, "Chiquita" an example of which is shown in FIG. 9. This screen shows previous medications administered to this animal as well as current, active medications, an example of which is Thiazine, prescribed by Dr. Jones. At the bottom of the screen are the particulars associated with this current prescription so that the veterinarian knows what is being taken, how many doses have been received, as well as previous medications. At the top of the screen appears any alert conditions for this animal. In this example, the animal has allergies.

Figure 10:
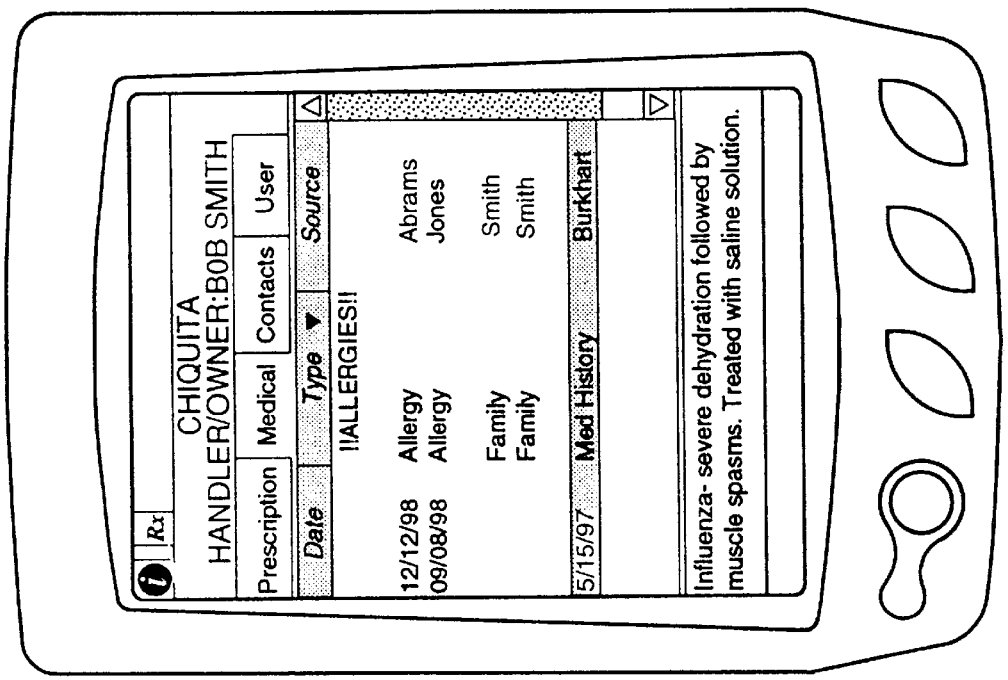
FIG. 10 is a medical history screen for the animal in FIG. 9 showing recent medical history from another veterinarian.

The second category of screens, Medical Information, is shown in FIGS. 10 and 11. The veterinarian typically taps the screen image of the category to pull up the Medical Information screen as shown in FIG. 10 and taps on the medical history input from Dr. Burkhart. At the bottom of this screen is provided a short description of the illness, Influenza, treated mainly by rehydration with saline solution.

In FIG. 11, the veterinarian has tapped on one of the family history entries provided by the handler/owner in FIG. 10 and on the liver disease entry on FIG. 11 to display the information that two distant relatives of the animal had hepatolinticular degeneration. Thus the data uploaded from the handler/owner component 104 not only includes medication history but also medical history provided both by veterinarians and by the handler/owner.

FIG. 12 illustrates the Contact screen for "Chiquita's handler/owner, Bob Smith. The veterinarian has tapped on the handler/owner's wife's emergency contact entry, and her contact information such as telephone numbers and address are shown below the list of contacts.

Figure 13:
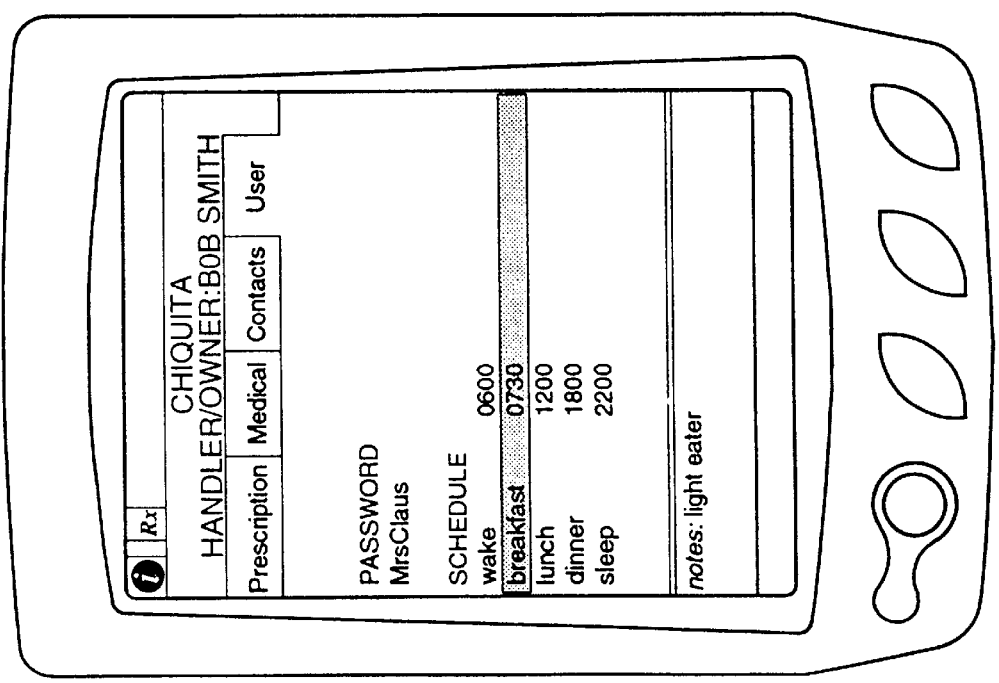
FIG. 13 is a user screen for the animal identified in FIG. 9 showing the animal's normal daily routines and any particular notes.
Figure 16:
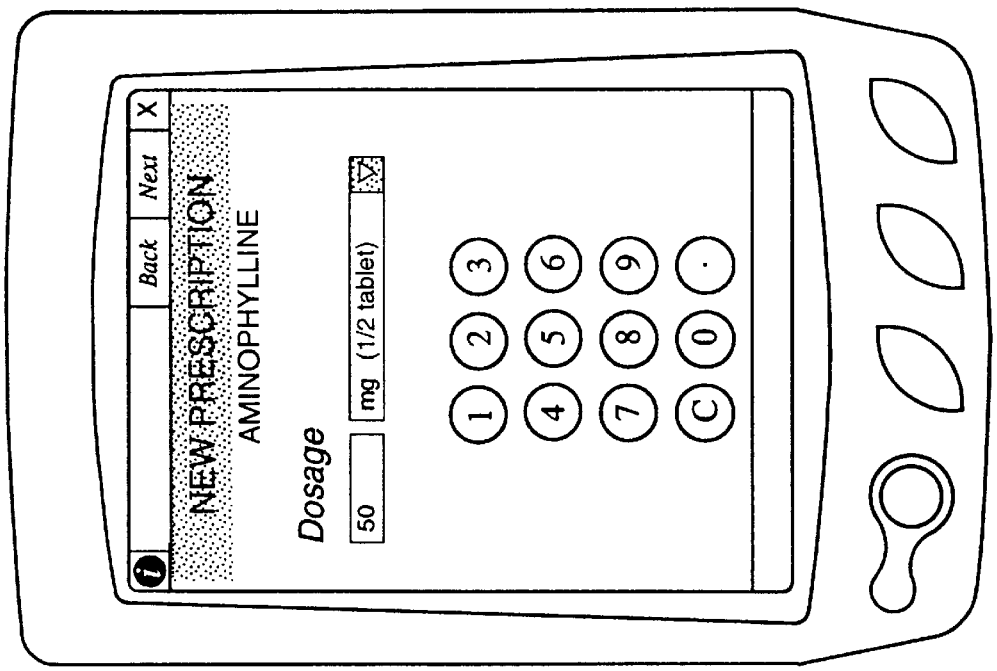
FIG. 16 is a veterinarian's new dosage screen for the drug identified in FIG. 15.

FIG. 13 illustrates the handler/owner's user information such as his password for accessing and changing protected information that the handler/owner does not want to be accessible by anyone but the veterinarian, and his pet's habitual schedule information. This information will be considered by the scheduling program embedded in the handler/owner component in order to optimally schedule the administration of medications in accordance with the handler/owner's general activity patterns. For example, Chiquita typically awakens with Bob Smith at 0600 and eats breakfast at 0700 and dinner at 1800 or 6pm. Therefore if a medication is to be administered to the animal twice daily, and does not require food to be taken at the same time, the program would schedule the drug to be taken at 0600 and 1800 rather than midnight and noon. If the drug must also be taken with meals, the program would then schedule the drug to be taken at 0700 and 1800 so as to be as close to 12 hours apart as possible but still at meals. Thus the information provided on the user screen as shown in FIG. 13 is an important consideration in the software scheduling of drug administration.

Figure 15:
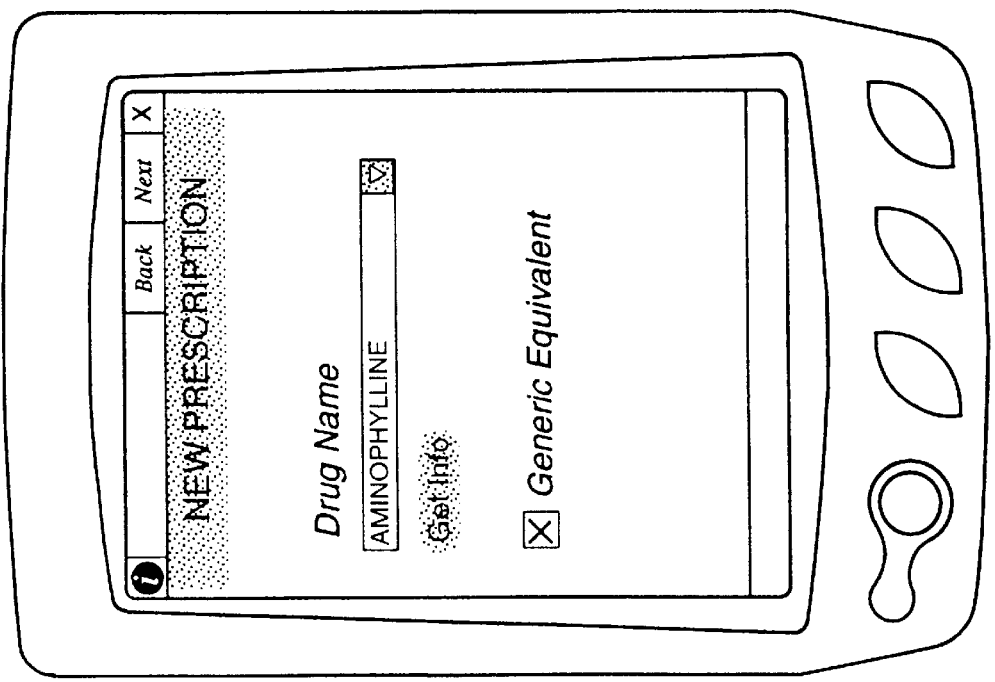
FIG. 15 is a veterinarian's new drug screen.
Figure 17:
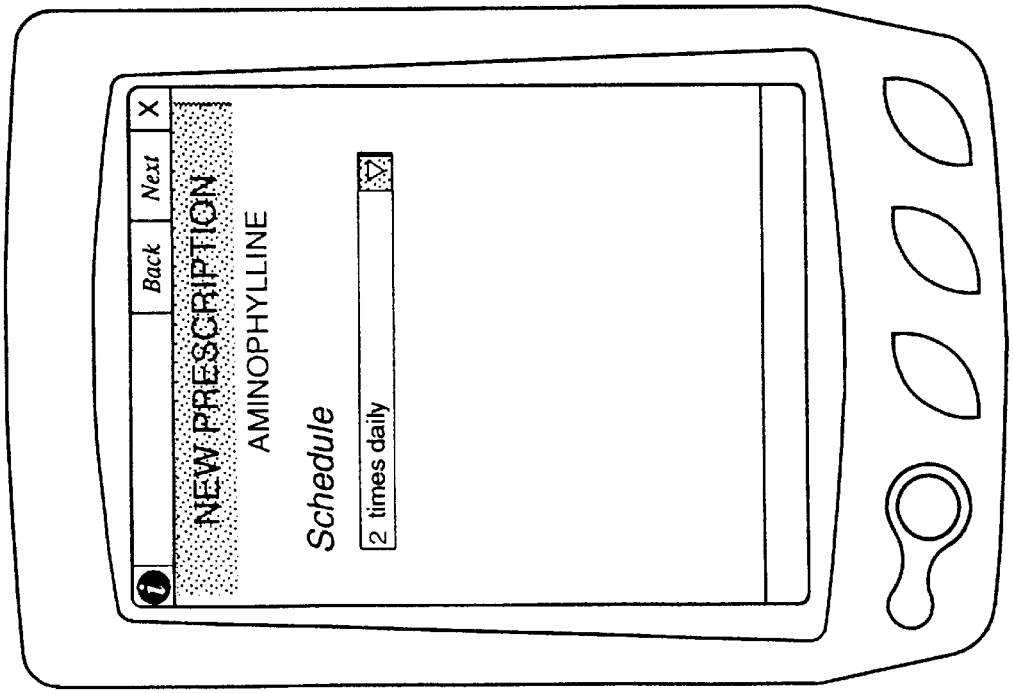
FIG. 17 is a veterinarian's new drug administering schedule screen for the drug identified in FIG. 15.

The screens shown in FIGS. 14 through 24 illustrate how the system in accordance with the present invention assists the veterinarian in prescribing medication to a handler/owner for administration to an animal. Assume that the veterinarian, Dr. Abrams in this example, decides to prescribe a new medication for Bob Jones' pet as shown on the screen in FIG. 14. The sequence begins in FIG. 15 with the veterinarian tapping on "NEW" back in FIG. 14. FIG. 15 pops into view. Here, the veterinarian component shows a list of drugs via a pull down menu. The veterinarian selects and taps on the desired medication, in this case, Aminophylline and taps on Generic Equivalent. The veterinarian then taps on "Get Info" and the screen of FIG. 16 pops up. The veterinarian can enter manually via the on screen keypad the desired dosage of Aminophylline, or alternatively select the available commercial dosage via a pull down menu in FIG. 16. After selecting or inputting the desired dosage, the veterinarian taps "next" at the top of the screen and the screen shifts to the schedule screen as shown in FIG. 17. Here the veterinarian can select the frequency of medication from a pull down menu.

Figure 18:
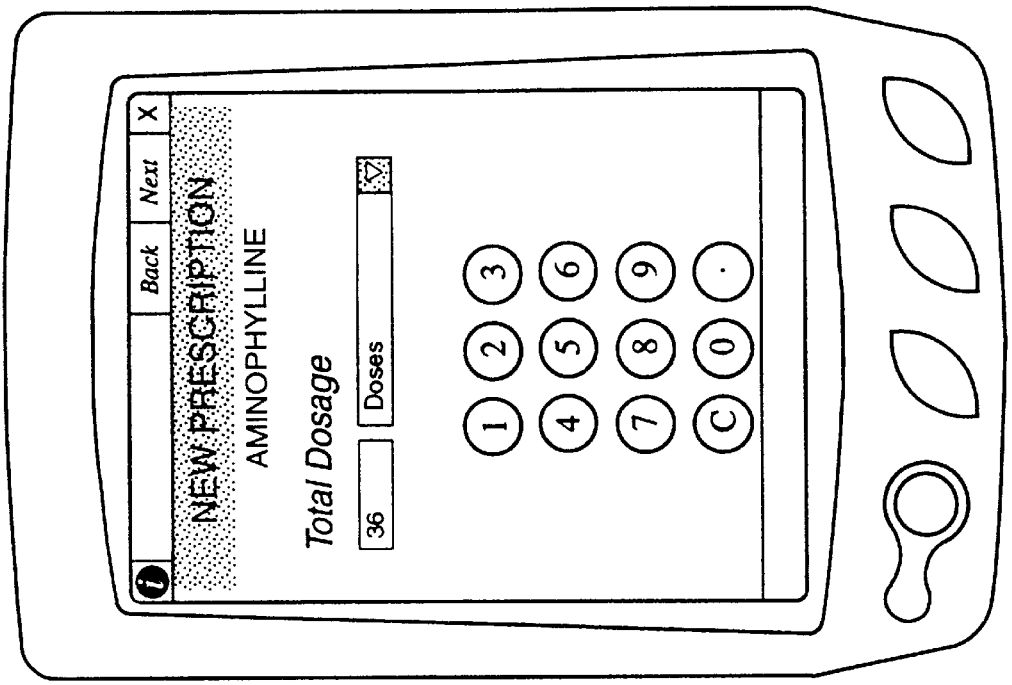
FIG. 18 is a veterinarian's new total dosage screen for the drug identified in FIG. 15.

Once the schedule is selected, the veterinarian taps on "next" and the screen automatically shifts to the total dosage screen, FIG. 18, where the veterinarian selects the number of doses, milliliters, ounces, etc. that may be required for the particular medication. Again, a keypad is provided on screen for the veterinarian to numerically enter the number of doses required.

Figure 20:
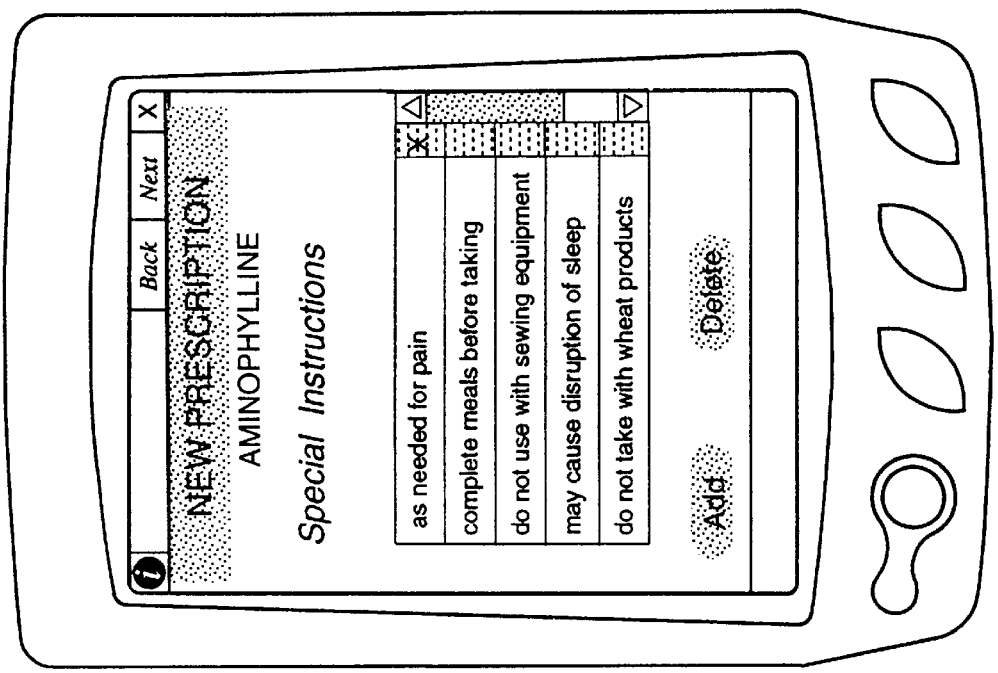
FIG. 20 is the veterinarian's new drug special instructions screen for the drug identified in FIG. 15 with a pull down menu expanded.
Figure 19:
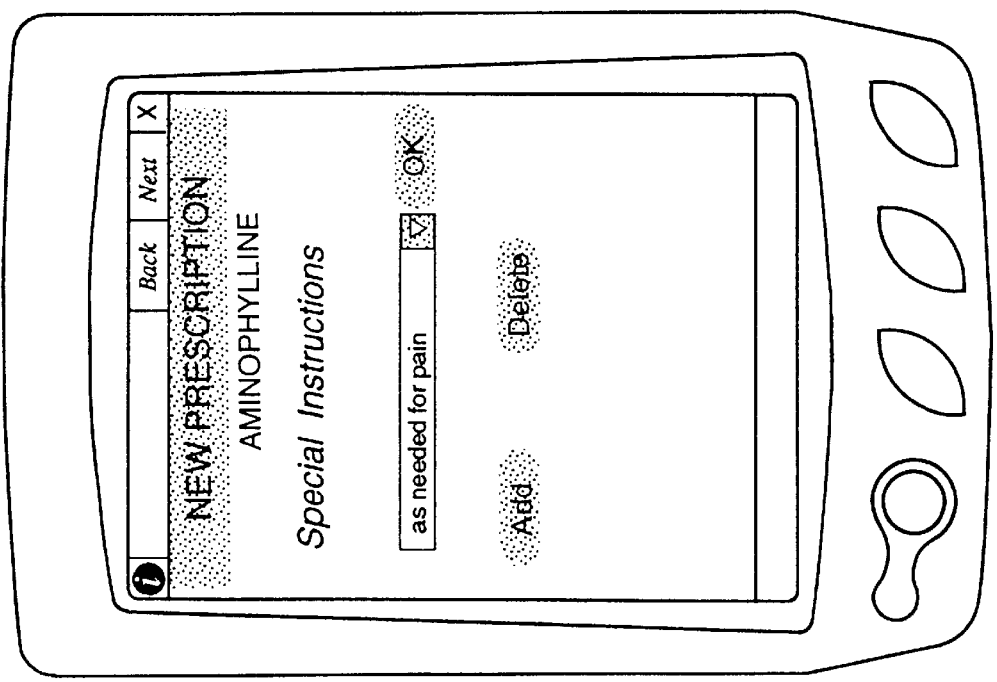
FIG. 19 is a veterinarian's new drug special instructions screen for the drug identified in FIG. 15.
Figure 22:
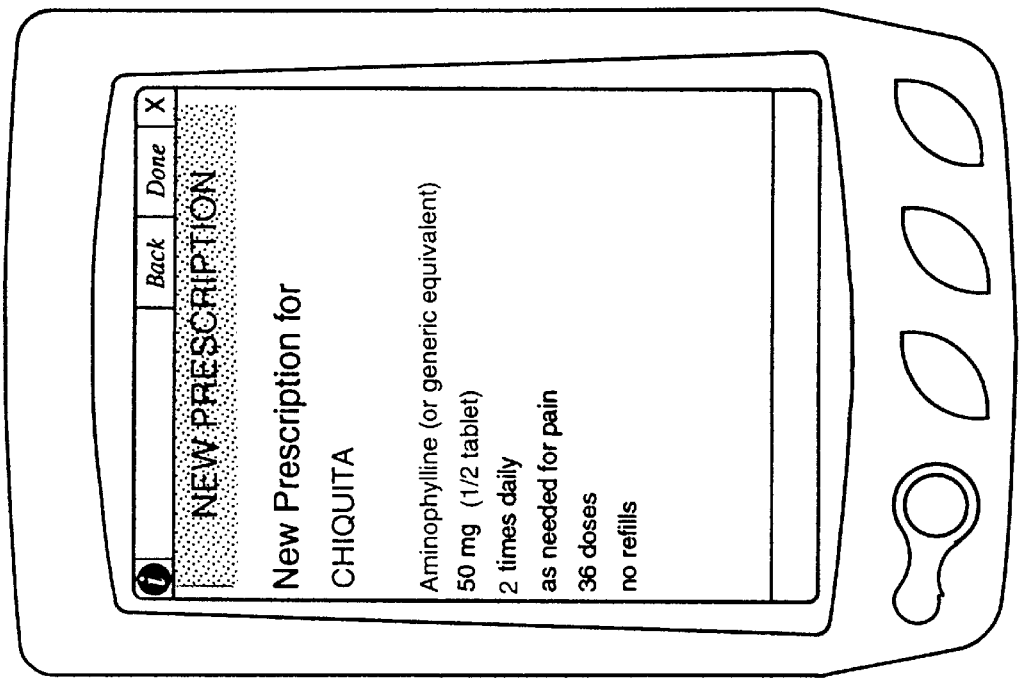
FIG. 22 is the veterinarian's summary new drug screen for the drug identified in FIG. 15.

When the total dosage has been selected the veterinarian taps on "next" at the top and the screen automatically shifts to that shown in FIG. 19 where special instructions may be selected from a pull down menu or manually entered. If the latter is the case, the veterinarian taps on "add" and a miniature keyboard appears which the veterinarian can utilize to add a customized entry. This entry will then be added to the database and the component may be directed to subsequently show this entry as a selectable option from the pull down list of special instructions as is shown in FIG. 20.

Figure 21:
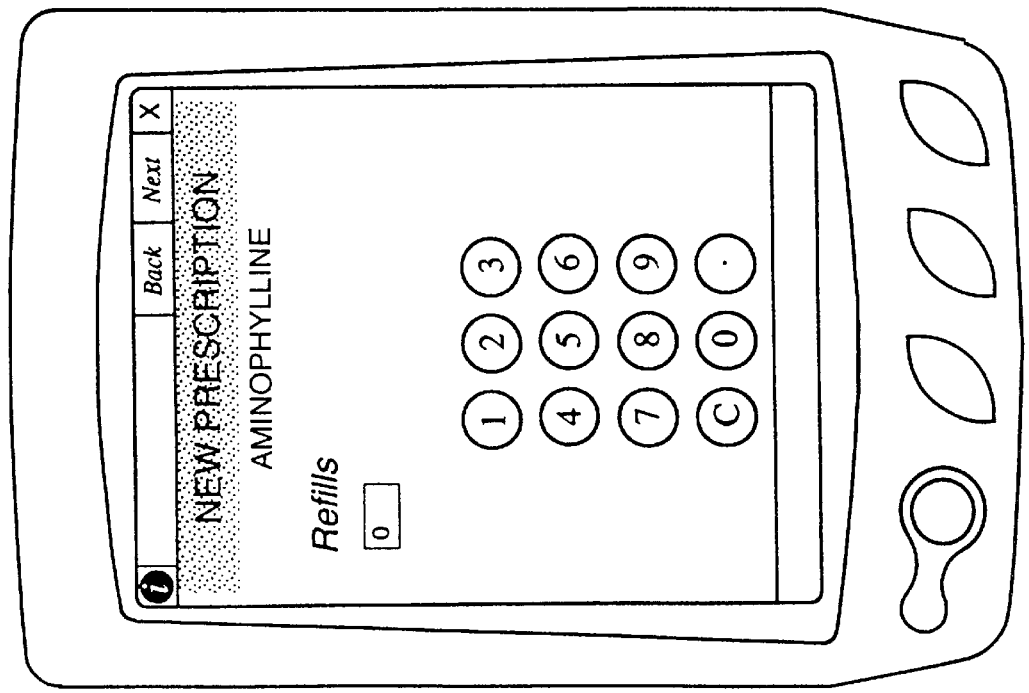
FIG. 21 is the veterinarian's new drug refill instruction screen for the drug identified in FIG. 15.
Figure 24:
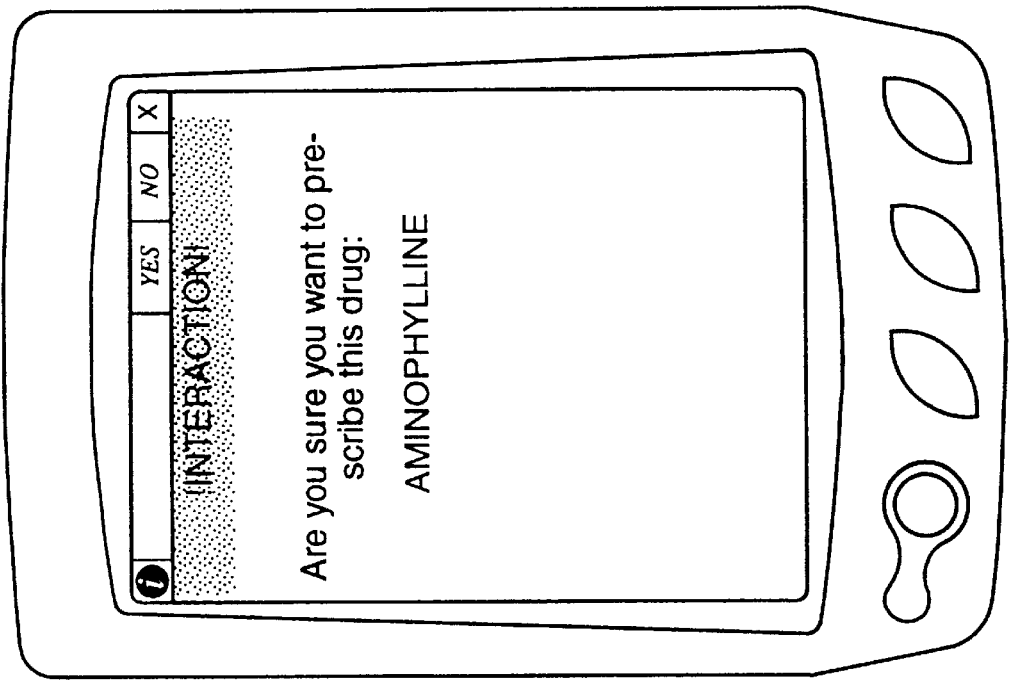
FIG. 24 is an exemplary potential interaction screen for the drug identified in FIG. 15.

When special instructions, if any, have been entered, the veterinarian taps on "next" and the screen shifts to the Refills screen shown in FIG. 21. Here the veterinarian enters the number of refills of the prescription that may be obtained from the veterinarian. The veterinarian then taps again on "next" and the screen then shifts to a summary of the new prescription shown in FIG. 22. If this new prescription is satisfactory, the veterinarian taps on "Done" at the top of the screen. Alternatively, if the veterinarian wants to modify the prescription, he can tap on "Back" to go to the desired screen to change the prescription in whatever manner he chooses.

If the veterinarian taps on "Done" then the processor queries a database resident in the veterinarian component 102 for cautions and interactions. If there are any cautions, they are shown as in FIG. 23 along with a "Cancel" or "Prescribe" query. If the veterinarian chooses "Prescribe", then any interactions in the caution screen will trigger a confirmation screen shown in FIG. 24. If the veterinarian chooses "yes" on this screen, then the prescription is added to the handler/owner database for Chiquita and downloaded to Bob Smith's handler/owner component 104 along with a confirmation security code of the prescribing veterinarian.

The veterinarian support component 106 in particular can be used to augment the information provided to the handler/owner component by adding more up to date administration cautions and instructions to the handler/owner component that normally are provided in small print today along with most prescriptions as they are filled. These instructions may include such things as not to take the medication with food, don't take more than three days in a row, etc. In addition, the veterinarian support component may flag additional potential drug interactions that may have been more recently identified as pertinent to the animal or to humans by the medical and pharmaceutical community.

Potential interactions may be detected by the veterinarian component 102. Identified cautions or potential interactions flagged by the software routine in the Veterinarian component are displayed to the veterinarian prior to confirmation of the prescription as exemplified by the screen in FIG. 23. Similarly, a check of potential interactions and cautions concerning a particular prescription is performed in the veterinarian support component 106. If an interaction is detected by the veterinarian or veterinarian support software, it warns the veterinarian of the severity of the interaction. The interaction check in the veterinarian's computer and in the veterinarian's component 102 serves a watchdog function only. The veterinarian has the ability to override the software warning and prescribe the drug anyway. This is routinely done by veterinarians today for minor potential interactions when substitute drugs are either unavailable or would cause even more severe interactions. In either case, the interaction is flagged in the handler/owner component 104 such that the handler/owner can review the interaction warning thus alerting the handler/owner that there is an interaction potential between two drugs. The handler/owner is then able to read about the interaction, usually in a brief form, and consult the veterinarian for more information if clarifications are needed. This capability in the handler/owner component 104 permits the handler/owner to make the most informed decision possible about his or her animal's medication and/or medication schedule.

The potential drug interactions primarily become extremely important in situations where a handler/owner needs to manage a large number of medications for an animal or set of animals simultaneously. Consequently, strict scheduling and sequencing of some of these drugs may be particularly important for optimized animal care.

Currently there is little general interaction data available concerning potential interactions between drugs when doses are delayed or skipped. However, the veterinarian may provide, through the veterinarian component 102, specific instructions to the handler/owner in these cases. This information may appear as separate potential interaction warnings or may actually be introduced into the handler/owner component scheduler software so as to pop up if the handler/owner attempts to postpone, delay or skip administering medication doses to the animal. The handler/owner component will track and monitor a handler/owner's track record for administering medications. Assuming that the handler/owner accurately records medications consumed on the handler/owner component, via requested responses, when medication is administered, the handler/owner component data may be helpful to the prescribing veterinarian in determining the effectiveness of a particular line of treatment. This data, for experimental drugs, may also prove extremely valuable to drug companies as well as the veterinarians in determining whether a drug regimen is or is not successful.

Figure 44:
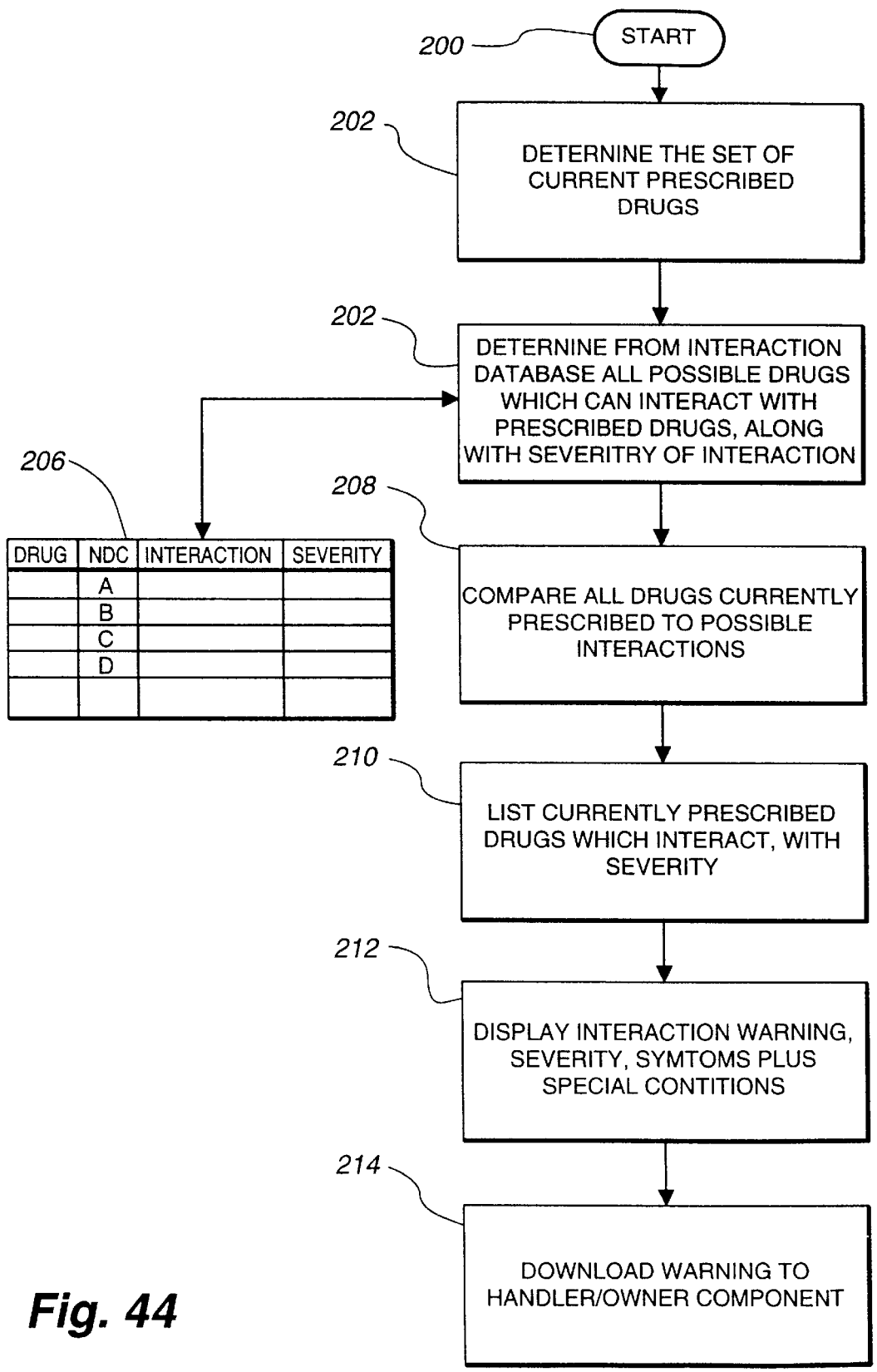
FIG. 44 is a simplified flow diagram of the drug interaction identification process according to one embodiment of the present invention.

The potential drug interaction software routine utilized by the veterinarian component 102 and/or the veterinarian support component 106 is shown generally in FIG. 44. This software routine may also be provided in the handler/owner component 104 or a simplified version provided in the handler/owner component 104. In the latter case, the routine may operate on a database contained in the handler/owner component 104 or may optionally be capable of tapping into a large mainframe database via modem and internet connection. This latter capability may be optimally utilized when the handler/owner desires to include OTC medication information in the handler/owner component 104 as the potential interactions for OTC drugs may be extensive compared to the individually prescribed prescription drugs prescribed to the handler/owner.

The veterinarian support component 106 may also be utilized to provide animal and handler/owner prescription information to and from the covering insurance organization for the animal, if any. In addition, as will be shown below, the handler/owner, while administering the medication, may identify and document interactions or side effects that can automatically be updated to the medical community through the veterinarian support component. This latter feature may be particularly valuable for experimental drugs utilized on a trial basis.

Figure 7:
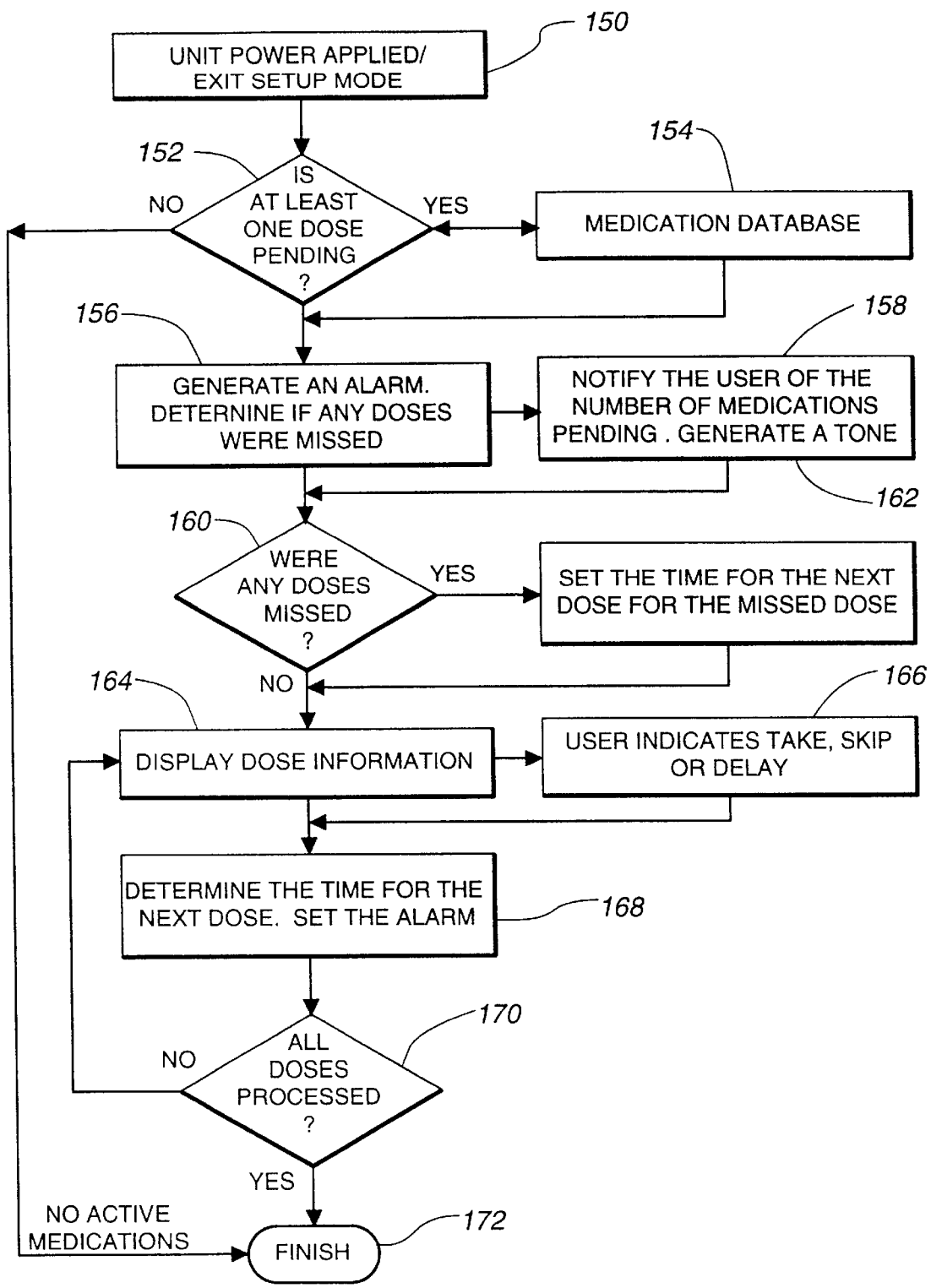
FIG. 7 is a flow diagram of a software scheduling example in the handler/owner component in accordance with the medication management system shown in FIG. 6.

FIG. 7 shows a flow diagram of the scheduler software utilized in the handler/owner component 104. As in the first embodiment 10 described above, the component 104 stays in a "sleep" mode to minimize power drain. In the sleep mode, only the alarm clock continues to operate. Upon generation of an alarm by the clock, or by the handler/owner pressing any one of the three buttons 116, 118, or 120, power is applied to the handler/owner component 104 in operation 150 and the LCD screen lights up and adjusts for optimum contrast depending on the ambient light conditions. The processor is then queried in operation 152 whether there is at least one dose pending. If yes, then the processor queries the prescription database 154 within the handler/owner component 104.

Every active prescription has a time and date tag indicating when the next dose is to be taken. The current time and date are compared to the time and date tag for each active prescription in the component's database. Pending doses are those having time and date tags equal to or less than the current time and date. If there is at least one dose pending, control transfers to operation 156 where an alarm is generated. The handler/owner component counts the number of medications having pending doses. Prescription time date tags are compared to the current time and date. If the difference in time between when the prescription should have been taken and the current time is greater than the allowable variance which is stored in the prescription information, the dose is logged as having been missed.

Missed medications are logged for each time that they were missed. A medication which is not taken within its allowable window is rescheduled for its next dose as if it were taken or skipped. This is to prevent doses from being taken too close together. The user will be prompted later to indicate whether missed doses were taken or skipped.

Once an alarm condition is generated in operation 156, a tone or other indication of the alarm is activated in operation 158. The handler/owner component 104 then displays the number of medications pending. Control then transfers to operation 160. The processor determines if any doses were missed in operation 160. If yes, control transfers to operation 162 where the time and date tag for the medication dose is set for the next dose for the missed medication. Control then transfers to operation 164.

If the answer in operation 160 is no, control transfers directly to operation 164 where the alarming dose information is displayed on the screen of the handler/owner component 104. The handler/owner then selects, in operation 166, whether to take, skip, or delay administration of the medication. Control then transfers to operation 168 where the time for the next dose is computed and tagged and the alarm set accordingly. Control then transfers to operation 170 which queries whether all doses pending have been processed. If so, control transfers to operation 172 where the handler/owner component returns to the sleep mode, awaiting the next alarm condition. If the answer to the query in operation 170 is no, then control transfers to operation 164 to display dose information for the next pending medication.

If the answer to the pending dose query in operation 152 above is no, signifying there are no doses pending, operation transfers directly to operation 172 where, after a predetermined period of time, the handler/owner component 104 returns to the sleep mode.

The time for the next dose for each active medication is calculated by adding the dosage interval to the current time. Doses which are delayed are postponed for ½ hour. Skipped doses are logged as missed, and the next dose alarm is set for the next interval as if the scheduled had been taken. The interval between doses is calculated depending on the requirements of the specific prescription. Dose intervals can be set as a fixed number of hours, or as a number of doses during each daily period. The interval would then be calculated by dividing the daily period by the number of doses to be taken each day. The daily period for each dose is determined as either the period of time during which the handler/owner is awake, or 24 hours if the prescription must be taken on a regular basis, even if the handler/owner is normally asleep. Additionally, the interval may be specified as occurring at a number of fixed times each day, such as the times when the user eats regular meals. The handler/owner's schedule is entered by the handler/owner and includes wake time, bed time, and the times of each regular meal (breakfast, lunch and dinner). Doses may be scheduled to occur on the handler/owner's schedule, or relative to the schedule. For example, a dose might be scheduled to be taken with lunch, or within ½ hour before of after lunch. Each time that a dosage is taken, the number of remaining doses is decremented. If no doses remain, the prescription is finished, the medication is removed from the pending dosage registers, and no additional alarms will be generated for that prescription.

Figure 25:
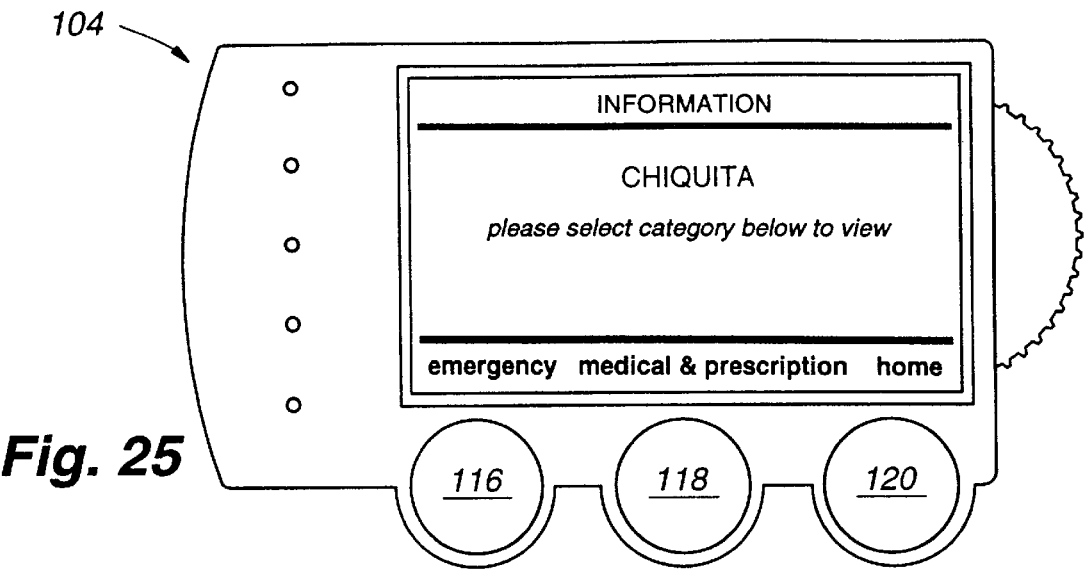
FIGS. 25 through 43 are a series of screens provided on the handler/owner component as a result of the new drug prescribed by the veterinarian and illustrated in FIG. 22.
Figure 26:
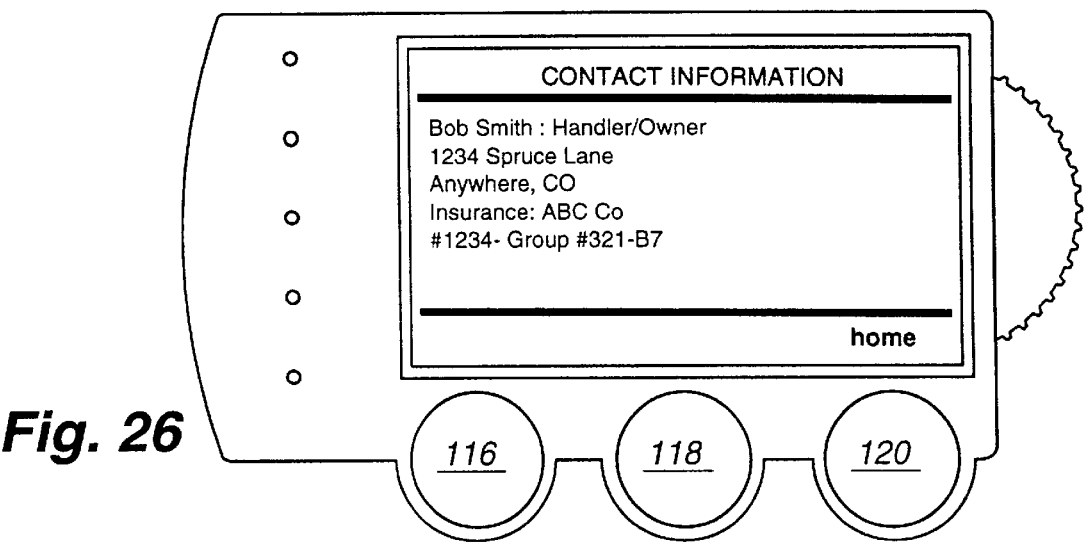

FIGS. 25 through 43 show exemplary information displayed on and controlled by the handler/owner component 104. In FIG. 25, a handler/owner has pressed one of the buttons 116, 118 or 120. The unit powers out of the sleep mode and a default screen is shown, requesting the handler/ owner to select one of the three options shown: emergency information, medical and prescription information, or home information FIG. 26 shows the information typically displayed upon the handler/owner selection of button 120. The information includes the handler/owner's name, address, and insurance information.

Figure 27:
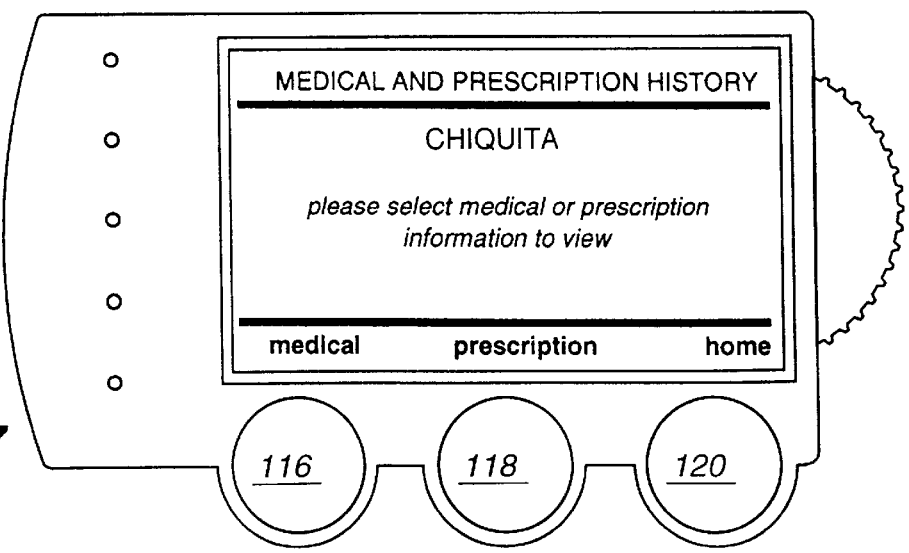

FIG. 27 shows the information displayed upon the handler/owner selection of button 118 in FIG. 25. This is a preliminary medical screen permitting the handler/owner to select between medical or prescription information.

Figure 28:
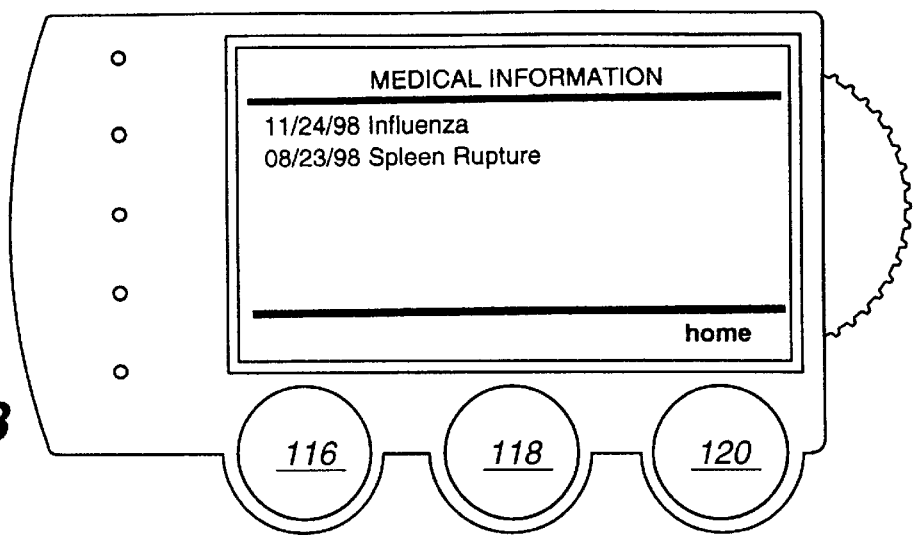

FIG. 28 shows the information displayed when the medical button 116 is pressed. It is a reverse chronological listing of medical conditions which have been entered in the handler/owner database.

Figure 29:
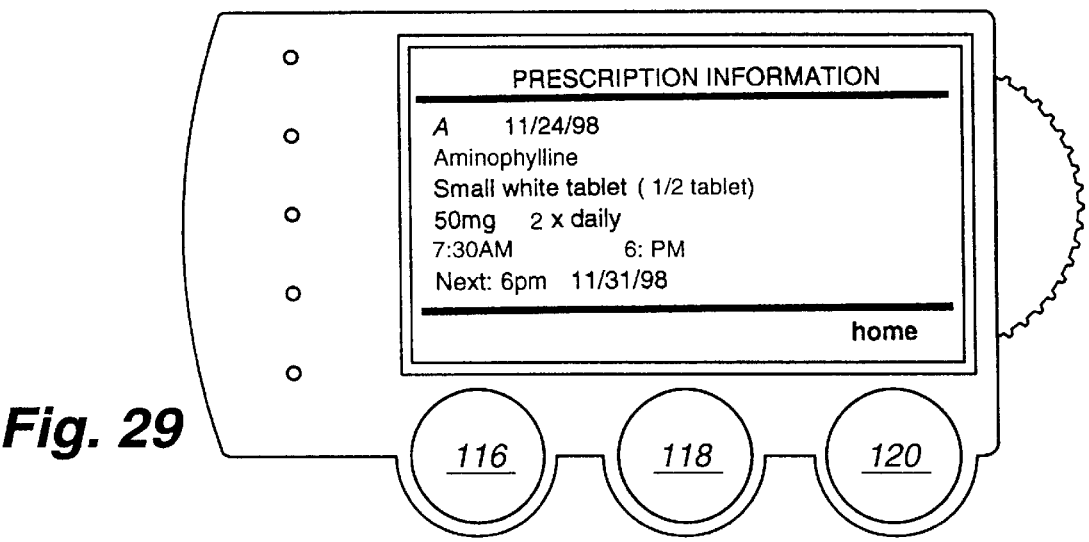

FIG. 29 shows the information displayed when the prescription button 118 is pressed. Again, a reverse chronological listing of prescriptions is displayed, setting forth the name of the drug, the dosage and frequency, a physical description of the drug such as a small white pill, the schedule, and when the next dose is presently scheduled to be administered.

Figure 30:
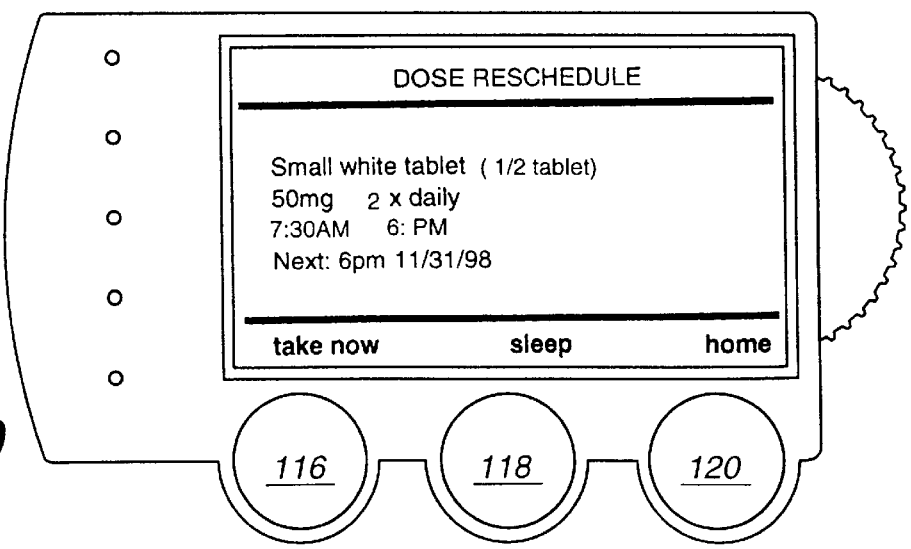
Figure 31:
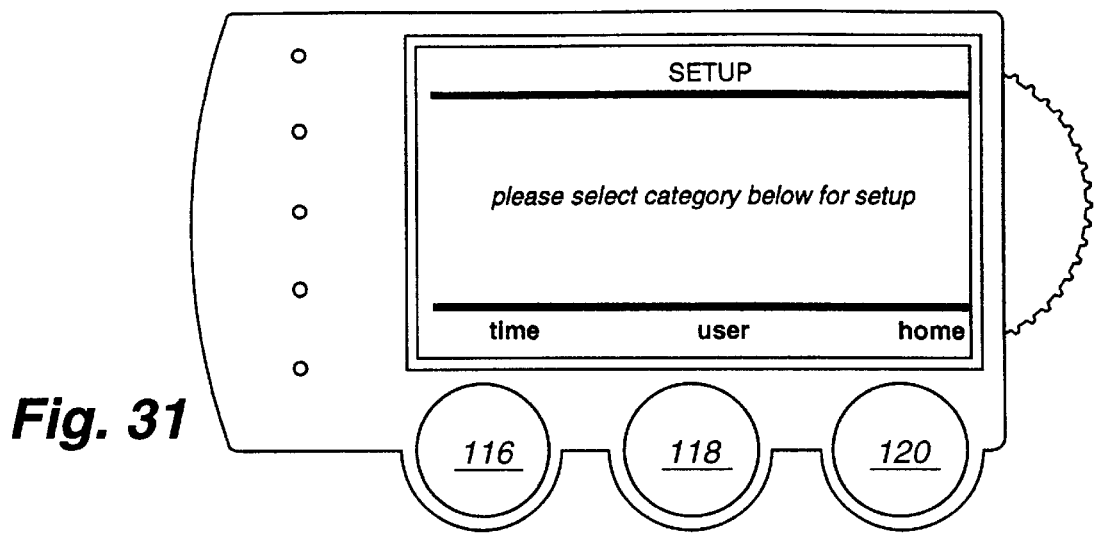

FIG. 30 shows the screen information when an alarm condition is activated. The display shows the drug name, physical description, dosage and frequency and schedule. Note that the three buttons 116, 118, and 120 now are labeled "take now", "sleep" and home.

FIGS. 31, 32, 33, 34, and 35 are self explanatory. These screens show setup information for setting the clock, password and personal schedule information.

Figure 36:
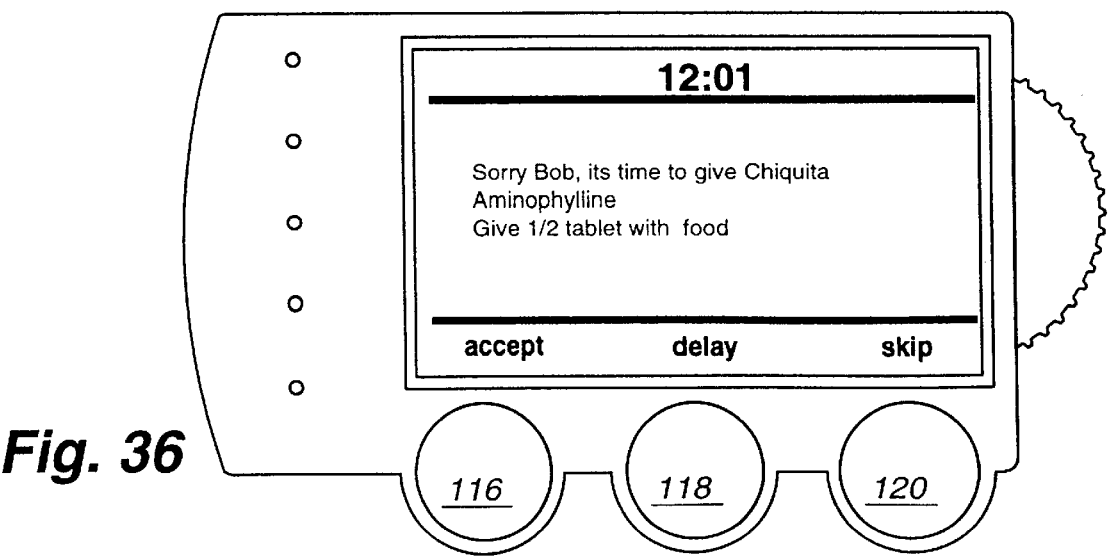

FIG. 36 refers back to FIG. 30 where an alarm condition has been activated. If the scheduling program determines that the medication cannot be delayed, because of other drug interactions or otherwise, the screen will continue to instruct the handler/owner to take the medication now, i.e. press the accept button 116. When the instruction is accepted, the time and date is logged and the next dose administration is displayed as in FIG. 37. Alternatively, if the dosage scheduled in FIG. 36 may be skipped but not delayed, the handler/owner presses the skip button 120 in FIG. 36 and the processor transfers to the screen shown in FIG. 38, and the skipped dosage is logged. Finally, if delay of administration of the dosage was permissible in FIG. 36, the delay is logged and the alarm reset for thirty minutes later. After two delay periods, the screen will be as shown in FIG. 39 if the medication is taken at that time.

Figure 37:
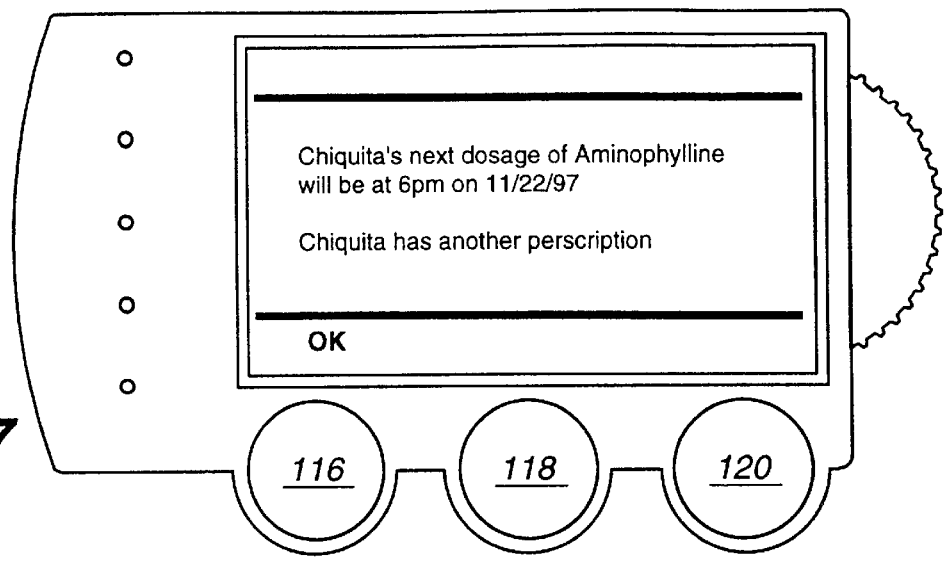
Figure 38:
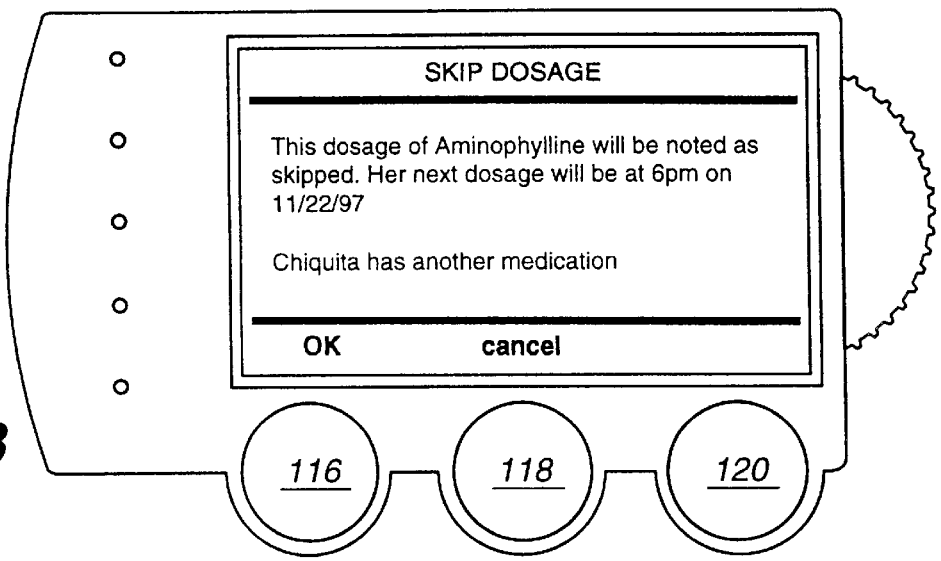
Figure 39:
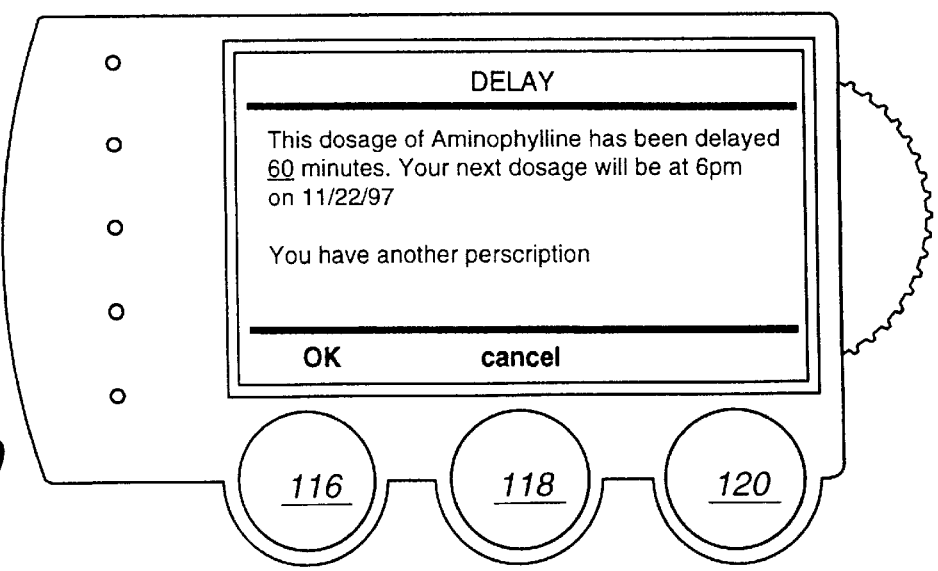
Figure 40:
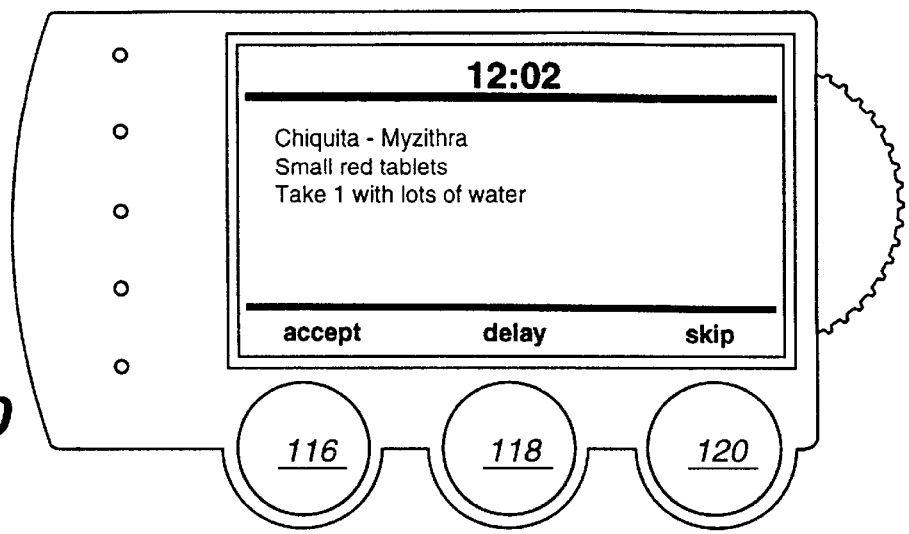
Figure 41:
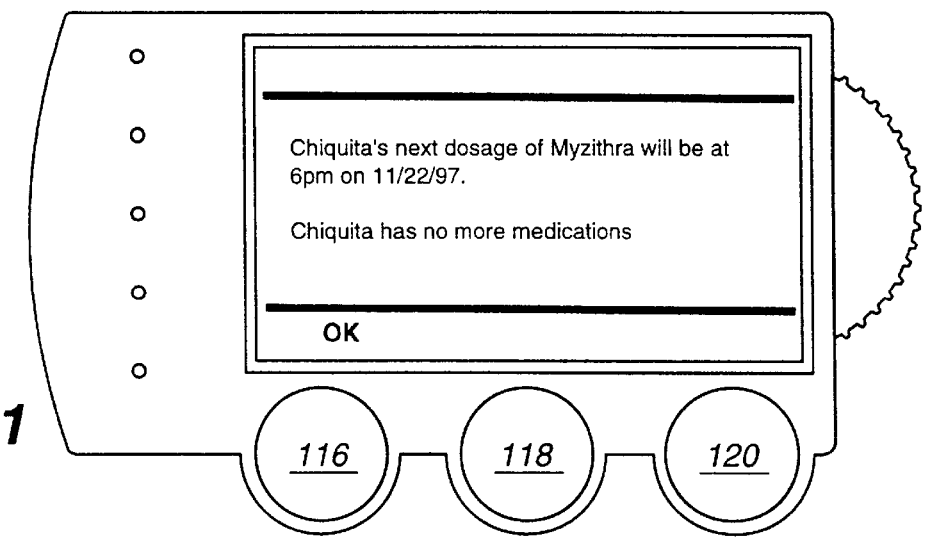
Figure 42:
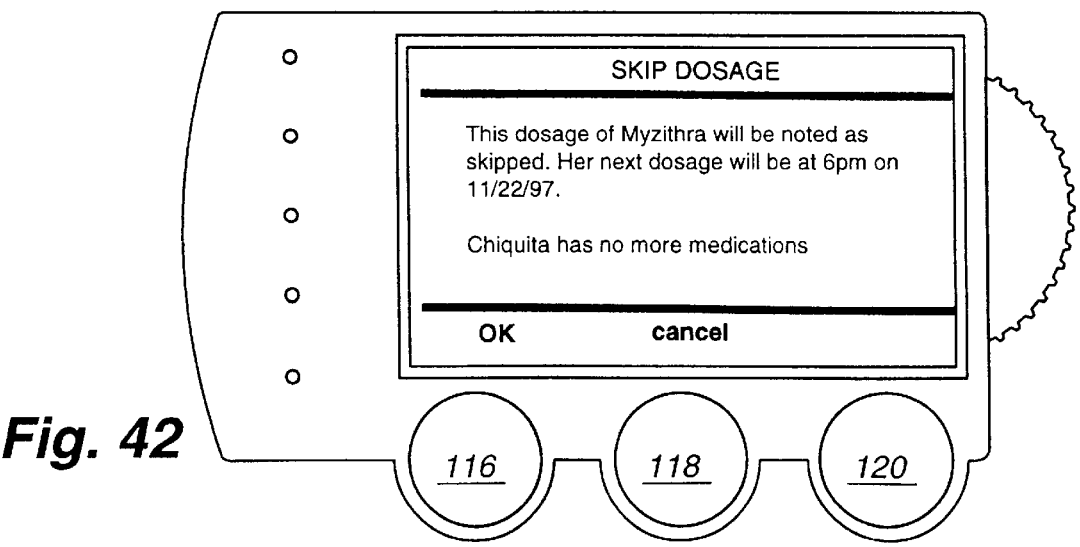
Figure 43:
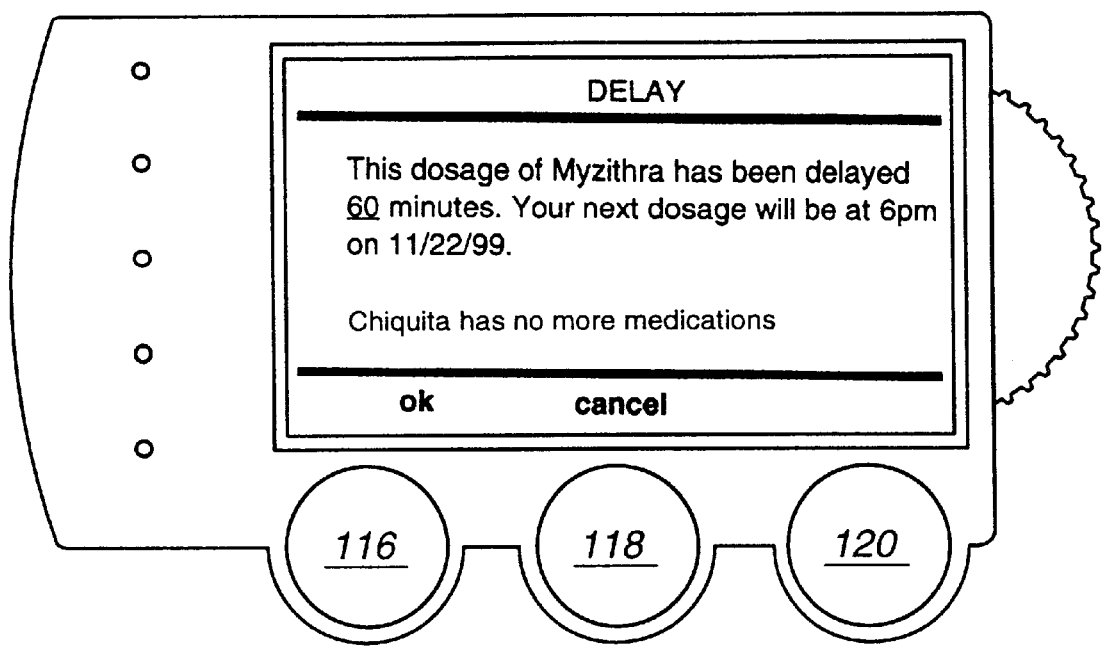

FIGS. 37 through 39 indicate that there is another drug that must be administered. After selecting OK in FIGS. 37, 38, or 39, the next drug is displayed as shown by example in FIG. 40. The process of proceeding through the screens is then repeated. For example, FIG. 41 shows the screen which appears if "accept" is chosen in FIG. 40. FIG. 42 shows the screen which appears if "skip" is chosen in FIG. 40. FIG. 43 shows the screen which appears of "delay" is chosen in FIG. 40.

A unique feature of the management systems 10 and 100 in accordance with the present invention is the capability for identification, evaluation and flagging of potential adverse interactions between prescribed drugs to each of the two or three parties to the medication administration triangle, the veterinarian, the veterinarian support database (PC), and the handler/owner. FIG. 44 is a simplified flow diagram of the drug interaction identification process according to one embodiment of the present invention. In the following description, the steps shown in FIG. 44 may preferably be performed by the veterinarian component 102 and/or the veterinarian support component 106. The results may be downloaded into the handler/owner component 104 in accordance with the veterinarian's discretion.

Figure 23:
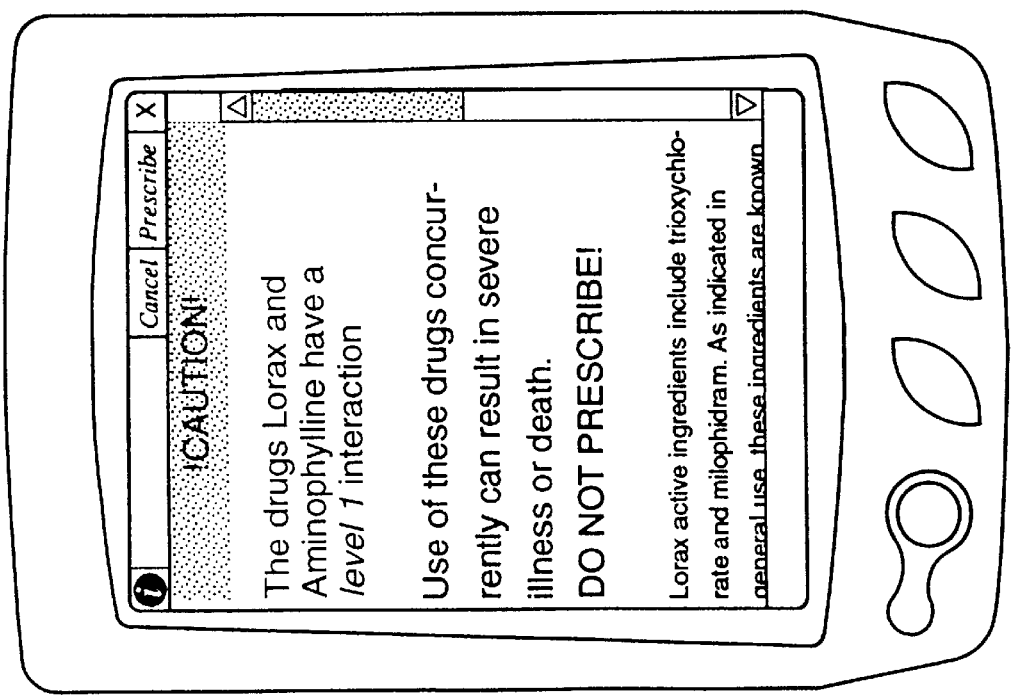
FIG. 23 is an exemplary caution screen for the drug identified in FIG. 15.

The present system is envisioned as including relational database tables of drugs in a relational database such as Microsoft Access which includes the drug names, their National Drug Code (NDC) numbers, if any, an interaction identifier, and a severity of interaction indicator for each identified interaction. For example, as is shown in FIG. 23, the drug Canderill is displayed as having a level 1 severity interaction with Lorax. The severity levels are envisioned as ranging from 1 to 5, with 1 being mild and 5 being deadly. As is shown in FIG. 23, level 1 severity is not absolutely mild. The concurrent use of these medications together can result in severe illness or death. However, the assignment of level 1 indicates that generally the interaction is of mild severity.

Referring now to FIG. 44, an exemplary interaction query begins in block 200 when the handler/owner component 104 interfaces with the veterinarian support component 106 in filling a prescription or when the veterinarian component 102 is used to prescribe a new drug to an animal whose handler/owner component 104 is coupled to the veterinarian component 102 as described above. In operation 202 the set of currently prescribed drugs is obtained by the program from the handler/owner component memory device. The program then jumps to operation 204 wherein the drug database 206, accessible via the veterinarian's computer or resident in the veterinarian component 102, is queried to determine all possible drugs which can interact with the set of prescribed drugs identified in operation 202. This set of possible drugs, along with their severity level of interactions, are then compared with the drugs currently prescribed to identify any possible interactions between the prescribed drugs in operation 208, Control then transfers to operation 210 where the currently prescribed drugs which interact, with their severity levels, are identified. Control then transfers to operation 212 where the interactions are sequentially displayed for the veterinarian, along with their severities, symptoms, special conditions or special qualifications. The veterinarian can then choose whether to download the interaction warnings to the handler/owner component in operation 214. Alternatively, the system may be designed to automatically download the interaction information to the handler/owner component 104.

The interaction testing scheme described above is a simple, two pass query system which is a binary interaction model where drug A reacts with drug B with a numeric severity code C. It cannot recognize or represent interactions between three or more drugs. The severity code of 1 to 5 representing 1 as a mild interaction and 5 as a potentially fatal interaction may be expanded in a number of ways. For example, symptomatic information may be included in the coding.

Future embodiments of the present invention are envisioned which include a rule based system created to model actual real world interactions on a more complex level. A table in such a relational database would contain a list of all known interactions, their severity, and symptoms. A related table would contain a list of conditions which must be met before the interaction could occur. These conditions might include such things as the substance, the dosages or drug concentrations, frequency of dose administration limitations, and conditional qualifiers. The qualifier "Mandatory", for example, would indicate that the condition must be met in order for an interaction to take place at all. This might be reserved for prescription drugs. A qualifier of "Potential" would indicate that the substance is not controlled or regulated, but could still cause an interaction if ingested. This could, for example, apply to over the counter medications, common or uncommon chemicals and herbal supplements.

In this case, to inquire whether or not an interaction could occur, a query would be run to determine which rules could potentially be filled by the handler/owner's prescription list or OTC medications. The resultant set is then processed sequentially to determine which, if any, rules have been met, and whether or not all of the mandatory rules have been met for any given interaction. Interactions for which all of the mandatory rules are met and for which any conditional rules exist are reported as interactions.

Figure 32:
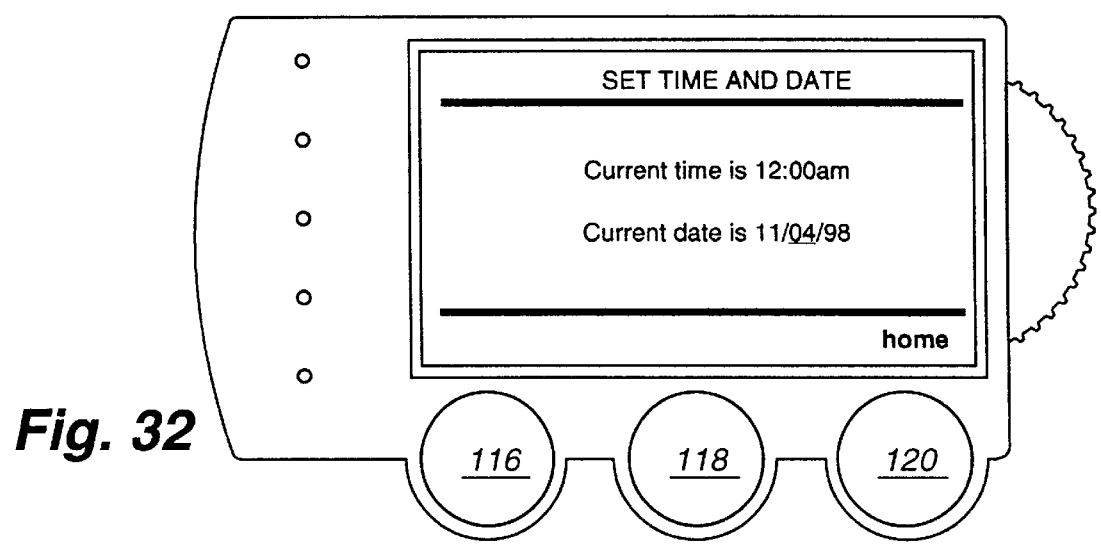
Figure 33:
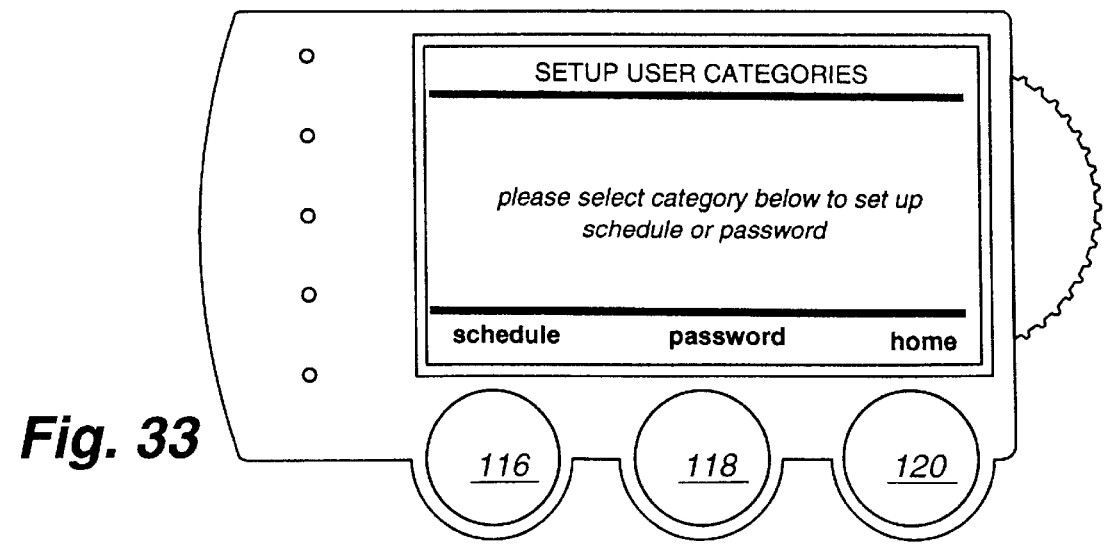
Figure 34:
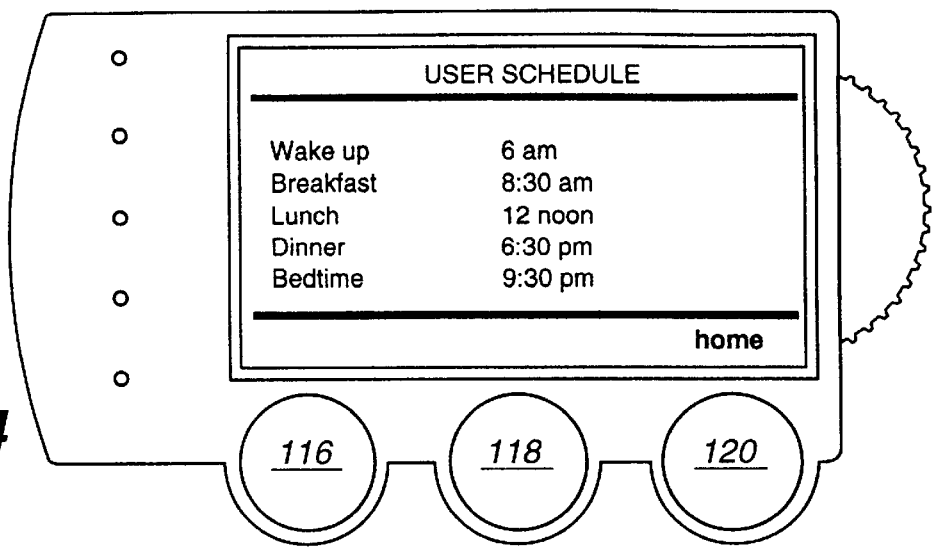
Figure 35:
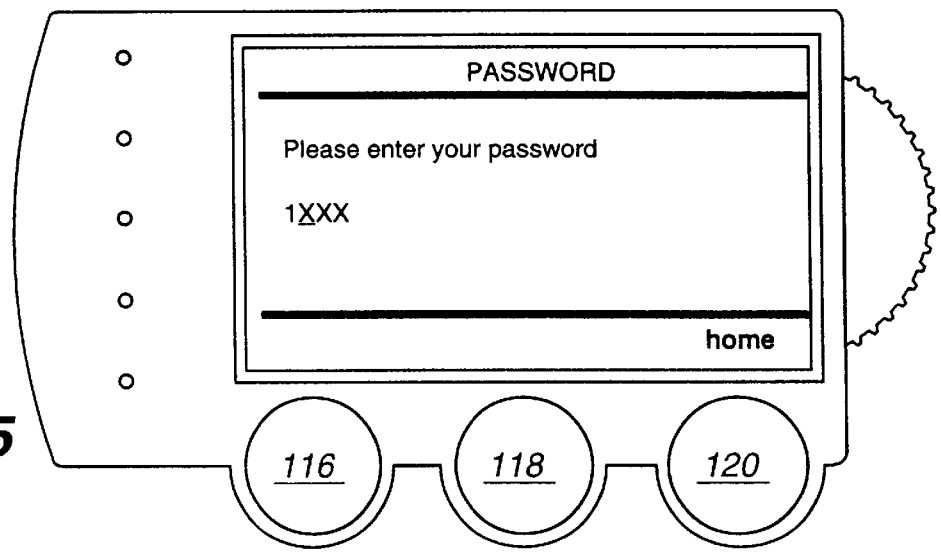

A veterinarian component 102 would then report the interaction, if identified, as shown in FIG. 32 above, and still permit the drug to be prescribed. If this drug is prescribed, a specific caution note would preferably be generated and downloaded to the handler/owner component 104 describing the interaction.

While there have been described above the principles of the present invention in conjunction with specific embodiments thereof, it is to be clearly understood that the foregoing description is made only by way of example and not as a limitation to the scope of the invention. For example, the housing 112 of the handler/owner component 104 may be further miniaturized and accommodated in a large wristwatch sized housing, with the buttons 116, 118, and 120 and wheel 124 provided by peripheral buttons around the housing and display like on a digital watch face. As in the second embodiment above described, the data contained in the database of the handler/owner component 104 would typically be transferred to and from the veterinarian support component 106 and the veterinarian component 102 via an infrared communication link as is conventionally known and used in some digital watches.

Another variation of the present invention may include the capability for the handler/owner to enter over the counter (OTC) medication data into the handler/owner component 104. This alternative would preferably also include internal storage for a database of potential interactions downloaded from the veterinarian component 102 or veterinarian support component 106 covering the particular medications inputted into the handler/owner component 104. The handler/owner can then enter the name and dosage amount as well as dosage frequency for any OTC medications that he or she may choose to consume. In this instance, the handler/owner component 104 would then query the scheduler and internal database of currently prescribed medications to determine whether there are any special instructions, cautions, or adverse interaction warnings that should be displayed to the handler/owner involving interaction of the OTC medication with prescribed medications.

Particularly, it is recognized that the teachings of the foregoing disclosure will suggest other modifications to those persons skilled in the relevant art. Such modifications may involve other features which are already known per se and which may be used instead of or in addition to features already described herein. It is also to be recognized that the interactions between prescription medications, OTC medications, herbal supplements, and other chemicals need not be detrimental to be identified. The databases utilized may include helpful or complementary interactions between such substances and the program utilized to identify and flag to the handler/owner, veterinarian those combinations of medications which are or may be enhanced by being administered in combination. The interaction identification program resident in the veterinarian support component 106, the veterinarian component 102 and/or the handler/owner component 104 may also be expanded to identify those combinations of three or more medications or chemicals which could precipitate an interaction that the handler/owner should consider. Although claims have been formulated in this application to particular combinations of features, it should be understood that the scope of the disclosure herein also includes any novel feature or any novel combination of features disclosed either explicitly or implicitly or any generalization or modification thereof which would be apparent to persons skilled in the relevant art, whether or not such relates to the same invention as presently claimed in any claim and whether or not it mitigates any or all of the same technical problems as confronted by the present invention. The applicant hereby reserves the right to formulate new claims to such features and/or combinations of such features during the prosecution of the present application or of any further application derived therefrom.

What is claimed is:

1. A Medication management system to assist a handler/owner control, monitor and manage administration of veterinarian prescribed medications and supplements to an animal comprising:
   a handler/owner component having data transfer interface and a retrievable database of said animal's medical history, prior prescribed medications, current prescribed medications, a potential adverse interaction between current prescribed medications, said handler/owner component being programmed to allow a user to modify a scheduled administration the scheduled dosage of medication; and,
   a veterinarian component having a retrievable veterinarian's database of medication information and an input/output device enabling a prescribing veterinarian to enter prescription information into the veterinarian component, said veterinarian's database being capable of receiving and storing handler/owner data and animal data transferred through said handler/owner component through said data transfer interface.

2. The system according to claim 1 wherein said handler/owner component includes a housing containing a microprocessor, a database, a display screen, a programmable alarm clock, and an input device for entering commands to said microprocessor and selecting information to be displayed on said display screen.

3. The system according to claim 2 wherein said handler/owner component comprises a generally rectangular plastic housing having a liquid crystal display screen and a plurality of control buttons accessible on an exterior of said housing.

4. The system according to claim 3 wherein said housing has a set of three control buttons positioned along one edge of said housing.

5. The system according to claim 2 wherein said veterinarian support component comprises a program and database resident in a veterinarian's personal computer.

6. The system according to claim 5 wherein each of said veterinarian and veterinarian support components communicates with said handler/owner component via an infrared interface.

7. The system according to claim 1 further comprising a veterinarian support component.

8. The system according to claim 1 wherein said veterinarian component is a personal digital assistant.

9. The system according to claim 1 wherein said handler/owner component includes a programmed alarm clock prompting a handler/owner to select whether to administer a medication dose, delay administering said medication dose, or skip administering said medication dose.

10. The system according to claim 9 wherein said handler/owner component program displays a warning to a handler/owner if said handler/owner selects a delay or skip of a particular medication dose that is impermissible in accordance with predetermined conditions.

11. The system according to claim 9 wherein the handler/owner component, after announcing an alarm condition, automatically logs time and date and whether a handler/owner selects administer, delay or skip for a particular medication dose.

12. The system according to claim 9 wherein said handler/owner component reschedules a subsequent alarm time for administration of a permissibly delayed medication dose.

13. The system according to claim 1 wherein the handler/owner component automatically logs the time and date of a handler/owner's response to each alarm for an administration of a medication dose and decrements a memory location containing a number representative of remaining doses of said medication.

14. The system according to claim 13 wherein said handler/owner component automatically terminates scheduling a medication dose when the total dosage of the medication has been administered.

15. A medication management system to assist a handler/owner control, monitor and manage administration of prescribed medications to an animal comprising:
 a handler/owner component containing a retrievable handler/owner database of animal medical history, prior prescribed medications and current prescribed medications, said handler/owner component including a display, a clock, a microprocessor, and a data transfer interface; and
 a veterinarian component having a retrievable veterinarian's database of medication information and an input/output device enabling a prescribing veterinarian to enter prescription information into the veterinarian component, said veterinarian's database being capable of receiving and storing animal and handler/owner data transferred from said handler/owner component through said data transfer interface.

16. The system according to claim 15 further comprising a veterinarian support component resident on a veterinarian's computer, said computer being adapted to interface with said handler/owner component to receive medication prescription data from said veterinarian component via said handler/owner component.

17. The system according to claim 16 wherein said veterinarian support component is a program resident in a veterinarian's personal computer.

18. The system according to claim 16 wherein each of said veterinarian and veterinarian support components communicates with said handler/owner component via an infrared interface.

19. The system according to claim 16 wherein said veterinarian component and/or said veterinarian support component includes a subroutine to identify potential interactions between a new medication being prescribed to an animal and a medication currently prescribed and administered to said animal.

20. The system according to claim 15 wherein said handler/owner component includes a housing containing an LCD display screen and an input device for entering commands to said microprocessor and selecting information to be displayed on said display screen.

21. The system according to claim 20 wherein said handler/owner component is sized to be hand held by a handler/owner.

22. The system according to claim 21 wherein said handler/owner component comprises a generally rectangular plastic housing having a liquid crystal display screen and a plurality of control buttons accessible on an exterior of said housing.

23. The system according to claim 22 wherein said housing has a set of three control buttons positioned along one edge of said housing.

24. The system according to claim 15 wherein said veterinarian component is a personal digital assistant having a Microsoft Windows type of operating system therein.

25. The system according to claim 15 wherein said handler/owner component includes a programmed alarm clock permitting a handler/owner to select whether to administer a medication dose, delay administering said medication dose, or skip administration of said medication dose.

26. The system according to claim 25 wherein said handler/owner component includes an internal a program which displays a warning to a handler/owner if said handler/owner selects a delay or skip of a particular medication dose that is impermissible in accordance with predetermined conditions.

27. The system according to claim 25 wherein said handler/owner component reschedules a subsequent alarm time for administration of a permissibly delayed medication dose.

28. The system according to claim 25 wherein the handler/owner component, after announcing an alarm condition, automatically logs time and date and whether a handler/owner selects administer, delay or skip for a particular medication dose.

29. The system according to claim 15 wherein the handler/owner component automatically logs the time and date of a handler/owner's response to each alarm for an administration of a medication dose and decrements a memory location containing a number representative of remaining doses of said medication.

30. The system according to claim 29 wherein said handler/owner component automatically terminates scheduling a medication dose when the total dosage of the medication has been administered.

31. The system according to claim 19 wherein a warning of said potential interaction may be selectively downloaded from either said veterinarian support component or said veterinarian component to said handler/owner component for display on said handler/owner component display screen when an alarm condition occurs for a medication associated with said potential interaction.

32. An apparatus for tracking, monitoring, and scheduling an administration of a plurality of medications to an animal and warning of an adverse interaction related to one or more of said medications comprising:
 a handler/owner component having generally rectangular hollow plastic housing containing a liquid crystal display, an alarm clock, a microprocessor, a power supply, an input device and a data transfer device, said housing being adapted to receive therein a removable memory device having a database resident thereon, said data transfer device being connectable to said removable memory device in order to display data stored on said removable memory device, including a warning of the adverse interaction related to one or more of said medications, and transfer scheduling information on said plurality of medications to said microprocessor.

33. The apparatus according to claim 32 further comprising a veterinarian component adapted to receive and program said removable memory device with prescription information and medical information.

34. The apparatus according to claim 33 wherein said smart card is adapted to be read in a veterinarian's computer in order to transfer prescription information from said veterinarian component via said smart card.

35. The apparatus according to claim 34 wherein said veterinarian component and said veterinarian's computer are each programmed to process prescription information against at least one medication database to identify potential adverse medication interactions and selectively download an interaction warning to said memory device for subsequent display on said handler/owner component.

36. The apparatus according to claim 32 wherein said input device includes a plurality of buttons on said housing for selecting between options presented on said display.

37. The apparatus according to claim 36 further comprising a rocker wheel switch on said housing for scrolling through one or more display screens on said liquid crystal display.

38. The apparatus according to claim 32 wherein said handler/owner component further comprises a database containing potential adverse medication interactions between a prescribed medication and an over-the-counter medication, said over-the-counter medication's identity being entered by a user, and said handler/owner component being programmed to compare prescription medication interaction information to over-the-counter medication interaction information.

39. The apparatus according to claim 32 wherein said handler/owner component is programmed to allow a user to modify the scheduled administration of the scheduled dosage of medication.

40. The apparatus according to claim 39 wherein the handler/owner component is programmed to reschedule the administration of said dosage of medication when the user modifies the scheduled administration of said dosage of medication.

41. The apparatus according to claim 39 wherein the handler/owner component is programmed to prohibit the user from modifying the scheduled administration of said dosage of medication when a possible adverse interaction may result from the modification.

42. The apparatus according to claim 40 wherein the handler/owner component is programmed to reschedule the administration of said dosage of medication according to the possible adverse interaction with a previous dosage of medication or a subsequent dosage of medication.

43. The apparatus according to claim 40 wherein the handler/owner component is programmed to reschedule a subsequent dosage of medication when the user modifies the scheduled administration of said dosage of medication.

44. An apparatus for tracking and monitoring administration of a plurality of medications to an animal by an animal handler/owner, said apparatus including a handler/owner component, a veterinarian component and a veterinarian support component, said handler/owner component comprising:
a generally rectangular hollow plastic housing containing a microprocessor connected to a liquid crystal display, an alarm clock, a power supply, an input device, a handler/owner's database stored in a memory, a program for comparing a prescribed medication to a database of medications stored in said handler/owner component to identify an interaction between said prescribed medication and another medication, and a data transfer device, said data transfer device being connectable to said veterinarian component and/or said veterinarian support component to transfer scheduling information on said plurality of medications to said microprocessor.

45. The apparatus according to claim 44 wherein said veterinarian component contains a veterinarian's database of medications, a program usable by a veterinarian to prescribe one or more medications to a handler/owner, and a program for comparing said one or more medications with said veterinarian's database of medications to identify and display interactions between said one or more medications being prescribed and another medication.

46. The apparatus according to claim 45 wherein said veterinarian component is adapted to communicate said prescribed medication and said interaction to said handler/owner component via said data transfer device.

47. The apparatus according to claim 46 wherein each of said veterinarian component and said handler/owner component includes an infrared data transfer device for communicating data therebetween.

48. The apparatus according to claim 44 wherein said veterinarian component contains a database of medications, a program usable by a veterinarian to prescribe one or more medications to a handler/owner and download said prescribed medication to said handler/owner component.

49. The apparatus according to claim 48 wherein one of said handler/owner component, said veterinarian component, or said veterinarian support component includes a program for comparing a prescribed medication to a database of medications to identify and display at least one interaction identified between said prescribed medication and another medication.

50. The apparatus according to claim 49 wherein said veterinarian support component has access to said database of medications and said program for comparing a prescribed medication to said database.

51. The apparatus according to claim 44 wherein said veterinarian support component is a software program resident on a veterinarian's computer, said program including a program for comparing said one or more medications with a database of medications to identify and display interactions between said one or more medications being prescribed and another medication.

52. An apparatus for tracking and monitoring administration of a plurality of medications to an animal by an animal handler/owner, said apparatus comprising:
a veterinarian support component;
a veterinarian component having a database of medications, a program usable by a veterinarian to prescribe one or more medications to a handler/owner and download said prescribed medication to said handler/owner component; and,
a handler/owner component, having a generally rectangular hollow plastic housing containing a microprocessor connected to a liquid crystal display, an alarm clock, a power supply, an input device, a handler/owner's database stored in a memory, and a data transfer device, wherein said data transfer device is connectable to said veterinarian component and/or said veterinarian support component to transfer scheduling information on said plurality of medications to said microprocessor, and said handler/owner component includes another program for comparing a prescribed medication to a database of medications stored in said handler/owner component to identify an interaction between said prescribed medication and another medication; and,
wherein one of said handler/owner component, said veterinarian component, or said veterinarian support component includes a program for comparing a prescribed medication to a database of medications to identify and display at least one interaction identified between said prescribed medication and another medication.

53. An apparatus for tracking and monitoring administration of a plurality of medications to an animal by an animal handler/owner, said apparatus comprising:

a veterinarian support component, wherein said veterinarian support component is a software program resident on a veterinarian's computer, said program including a program for comparing said one or more medications with a database of medications to identify and display interactions between said one or more medications being prescribed and another medication;

a veterinarian component; and a handler/owner component, having a generally rectangular hollow plastic housing containing a microprocessor connected to a liquid crystal display, an alarm clock, a power supply, an input device, a handler/owner's database stored in a memory, and a data transfer device, said data transfer device being connectable to said veterinarian component and/or said veterinarian support component to transfer scheduling information on said plurality of medications to said microprocessor, and wherein said handler/owner component communicates an animal's current prescribed medication data to one or more of said veterinarian support component and to said veterinarian component through an infrared data transfer device.

54. The apparatus according to claim 53 wherein said handler/owner component database includes current medications and current medication dose schedules for said animal.

55. The apparatus according to claim 54 wherein said handler/owner component stores and tracks in said database a handler/owner's responses to an alarm for administration of a medication to said animal.

56. The apparatus according to claim 55 wherein said handler/owner component can optimize scheduling of administration of medication to an animal based on said handler/owner's daily schedule of activity.

* * * * *